US012616476B2

(12) United States Patent
Zeiner et al.

(10) Patent No.: US 12,616,476 B2
(45) Date of Patent: May 5, 2026

(54) MECHANICAL FIXATION OF AN IMPLANTABLE ADJUNCT TO A STAPLE CARTRIDGE

(71) Applicant: CILAG GMBH INTERNATIONAL, Zug (CH)

(72) Inventors: Mark Zeiner, Loveland, OH (US); Christopher Q. Seow, Cincinnati, OH (US); Sarah A. Scully, Cincinnati, OH (US); Richard L. Leimbach, Cincinnati, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 0 days.

(21) Appl. No.: 18/921,521

(22) Filed: Oct. 21, 2024

(65) Prior Publication Data

US 2026/0108246 A1 Apr. 23, 2026

(51) Int. Cl.
*A61B 17/072* (2006.01)
(52) U.S. Cl.
CPC ............... *A61B 17/07292* (2013.01); *A61B 2017/07271* (2013.01); *A61B 2017/07285* (2013.01)

(58) Field of Classification Search
CPC ................................................ A61B 17/07292
See application file for complete search history.

(56) References Cited

U.S. PATENT DOCUMENTS

| | | | | |
|---|---|---|---|---|
| 9,351,730 | B2 | 5/2016 | Schmid | |
| 9,693,777 | B2 * | 7/2017 | Schellin | ............... A61B 17/068 |
| 9,757,124 | B2 * | 9/2017 | Schellin | ........... A61B 17/07292 |
| 9,775,608 | B2 * | 10/2017 | Aronhalt | .............. A61B 17/105 |
| 11,154,297 | B2 | 10/2021 | Swayze | |
| 2014/0131419 | A1 * | 5/2014 | Bettuchi | .......... A61B 17/07292 |
| | | | | 227/176.1 |
| 2015/0238187 | A1 * | 8/2015 | Schellin | ............... A61B 17/068 |
| | | | | 227/180.1 |

* cited by examiner

*Primary Examiner* — Nathaniel C Chukwurah
(74) *Attorney, Agent, or Firm* — Troutman Pepper Locke LLP

(57) ABSTRACT

Systems and methods for mechanically fixing an implantable adjunct to a staple cartridge are disclosed. A suture secured at the proximal and distal ends of the staple cartridge applies is tensioned over an implantable adjunct to secure the adjunct to the deck of a staple cartridge.

21 Claims, 18 Drawing Sheets

MECHANICAL FIXATION OF AN IMPLANTABLE ADJUNCT TO A STAPLE CARTRIDGE

FIELD OF INVENTION

The present disclosure generally relates to fixation of implantable adjuncts to staple cartridges. More specifically, the present disclosure relates to mechanical fixation systems and methods for securing implantable adjuncts to staple cartridges.

BACKGROUND

Stapling is a crucial aspect of many surgical procedures, such as gastrointestinal, thoracic, and gynecological surgeries. Staple cartridges used in said stapling procedures may include an implantable adjunct on the deck of the cartridge. Care must be taken to ensure the implantable adjunct is properly attached to the deck so that it is not dislodged from the deck during shipment or during surgery before the adjunct is positioned at the treatment site.

SUMMARY

It is an object of the present designs to provide devices and methods to meet the above-stated needs. The designs can be for systems and devices for securing an implantable adjunct on a staple cartridge, while also preventing accidental removal of the adjunct from the staple cartridge by a user.

The instant disclosure describes a staple cartridge. The staple cartridge includes an elongate body. The elongate body includes a deck. The elongate body includes a longitudinal slot extending along a longitudinal axis from a proximal end toward a distal end of the elongate body. The elongate body defines a plurality of staple pockets, each of the staple pockets is accessible via an opening in the deck. The staple cartridge includes an implantable adjunct removably secured to the deck. The implantable adjunct includes a longitudinal groove which is aligned with the longitudinal slot of the elongate body. At least one suture is provided within a longitudinal groove of the implantable adjunct and secured at each of the proximal end and distal end of the elongate body.

The staple cartridge may further include a pan to support the elongate body. The pan may include hooks which secure the suture at the proximal end of the elongate body. The proximal end of the elongate body may further include a suture guide directing the suture into the longitudinal groove of the implantable adjunct. The suture guide may include a bottom surface angled relative to the deck to retain the suture in a desired position.

In some examples, the suture comprises a sleeve attached onto at least one end of the suture. A proximal end of the elongate body may include a recess to secure the sleeve to the elongate body. The recess is sized to form a press-fit or an interference fit with the sleeve.

In some examples, the proximal end of the elongate body includes a cavity to receive a collet. The collet has a first opening to receive a suture therethrough and restrict the suture from sliding back through the first opening. The cavity tapers inward toward the longitudinal slot such that the first opening of the collet clamps onto the suture as the collet moves toward the longitudinal slot.

In some examples, the distal end of the elongate body includes a cutting slot on an underside and the suture extends across the cutting slot. The cutting slot provides a space between the underside of the elongate body and the suture to accommodate a cutting instrument.

In some examples, two through holes extend through the distal end of the elongate body, and the suture is passed through the holes to secure the suture to the distal end of the elongate body.

In some examples, the distal end of the elongate body includes two side grooves. The suture is looped around the two side grooves to secure the suture to the distal end of the elongate body. The staple cartridge may also include a post provided distal to the two side grooves. The suture may wrap around the post for additional securement of the suture to the distal end of the elongate body. The post may also center the suture into the longitudinal groove of the implantable adjunct.

In some examples, the distal end of the elongate body includes a guide ledge to direct the suture into the longitudinal groove of the implantable adjunct.

In some examples, an implantable adjunct includes a mesh layer. The suture may rest on top of the mesh layer when provided in the longitudinal groove to secure the implantable adjunct to the deck of the elongate body of the staple cartridge. The suture is biased to one side of the longitudinal slot of the elongate body to prevent cutting of the suture by a knife passing through the longitudinal slot of the elongate body.

The instant disclosure describes a method of securing an implantable adjunct to a deck of an elongate body of a staple cartridge. The method includes placing the implantable adjunct onto the deck of the elongate body, securing a suture to a distal end of the elongate body, advancing the least one suture through a longitudinal groove and onto a mesh layer of the implantable adjunct, and securing the suture to a proximal end. The suture provides a tension force onto the mesh layer of the implantable adjunct, thereby securing the implantable adjunct to the deck of the elongate body.

Securing the suture to the distal end of the elongate body includes wrapping the suture around an underside of the distal end of the elongate body, such that the suture extends over a cutting slot provided on the underside of the distal end of the elongate body. The method may further include advancing a first end of the suture through a first side groove provided on the distal end of the elongate body, advancing a second end of the suture through a second side groove provided on the distal end of the elongate body, wrapping the first end of the suture around a post, and positioning the first end of the suture through the longitudinal groove and onto the mesh layer of the implantable adjunct. The method may also include wrapping the second end of the suture around the post, and positioning the second end of the suture through the longitudinal groove and onto the mesh layer of the implantable adjunct.

To secure the implantable adjunct to the deck, a first robotic arm may grip the first end of the at least one suture, advance the first end through the first side groove, wrap the first end around the post, and position the first end through the longitudinal groove of the mesh layer of the implantable adjunct. A second robotic arm may grip the second end of the at least one suture, advance the second end through the second side groove, wrap the second end around the post, and position the second end through the longitudinal groove of the mesh layer of the implantable adjunct.

Other aspects of the present disclosure will become apparent upon reviewing the following detailed description in conjunction with the accompanying figures. Additional features or manufacturing and use steps can be included as would be appreciated and understood by a person of ordinary skill in the art.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation. It is expected that those of skill in the art can conceive of and combine elements from multiple figures to better suit the needs of the user.

DETAILED DESCRIPTION

Figures 1A, 1B:
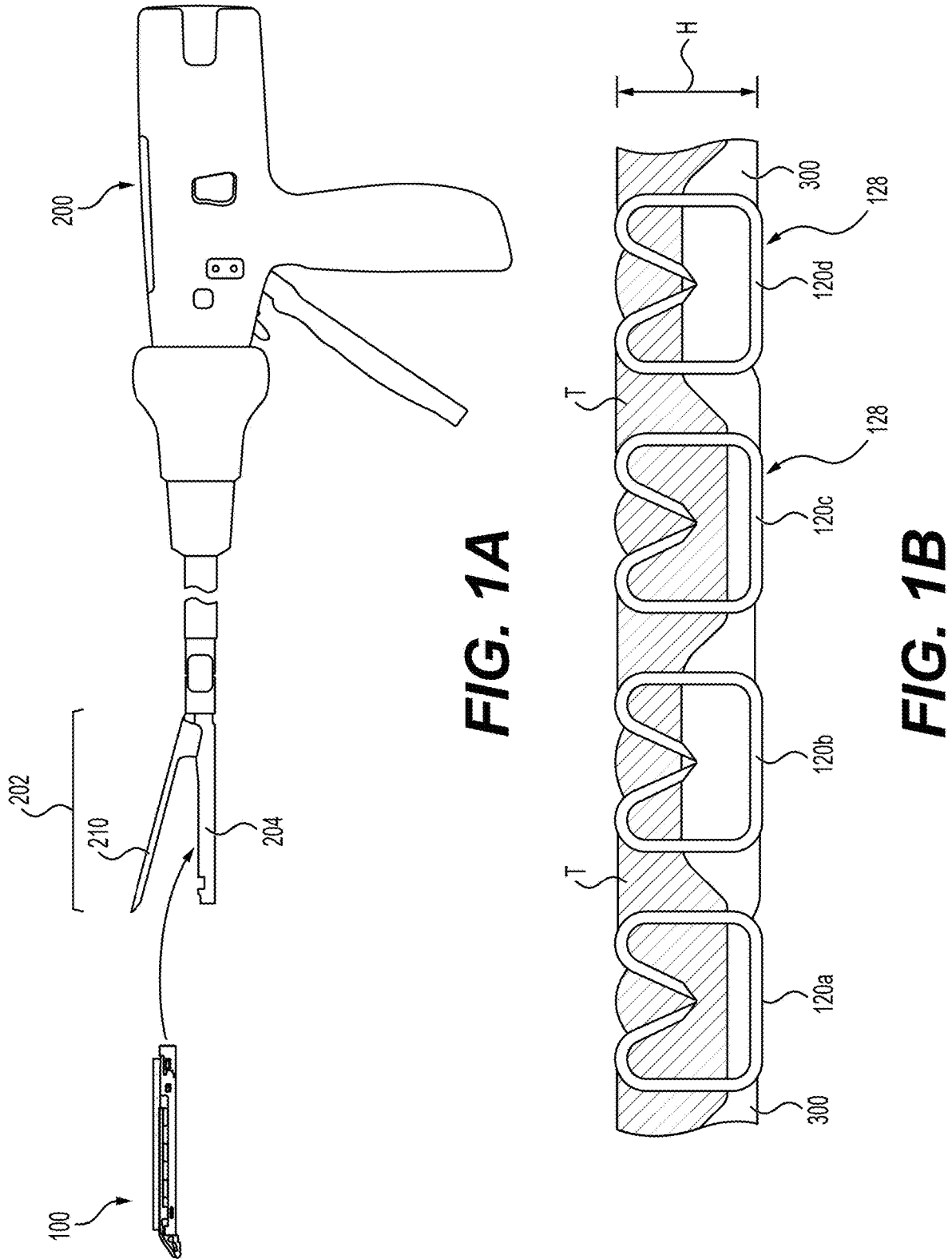
FIG. 1A is a side-view schematic of a staple cartridge being loaded into a surgical instrument, according to aspects of the present disclosure.
FIG. 1B is a schematic of an implantable adjunct stapled to tissue, according to aspects of the present disclosure.

Specific examples of the present invention are now described in detail with reference to the Figures, where identical reference numbers indicate elements which are functionally similar or identical. The examples provide solutions for staple cartridge systems that include an implantable adjunct. An implantable adjunct can be used in stapling surgery to account for differing tissue thicknesses across the length of the stapling surface. For instance, a length of tissue clamped in an end effector of a surgical instrument may by thicker at one end of the staple cartridge that at the other end. However, the staple cartridge may be loaded with staples of a single length, meaning the staples may be properly sized for the thicker section of tissue, but may be too long for the thinner section of tissue. If the staples are too long, proper compression of the tissue at the staple site may be compromised, leading to undesired bleeding. An implantable adjunct can account for this differing tissue thickness by providing support for the thinner sections of tissue. Where the tissue is thick, the implantable adjunct can be compressed all the way down since no additional thickness is needed to account for the staple length. Where the tissue is thin, the implantable adjunct is not as compressed, meaning the adjunct provides the additional thickness needed to account for the staple length, thereby providing proper compression in that section of the tissue.

The implantable adjunct must be properly attached to the deck of the staple cartridge so that it does not become dislodged during shipment or, importantly, during the surgical procedure. For instance, during surgery the staple cartridge is loaded into an end effector of a cutter/stapler surgical instrument, sent through a cannula to a surgical site, traversed through and around tissue, and then positioned at the target tissue site that will be cut and stapled by the surgical instrument. If the implantable adjunct is not properly attached to the deck of the staple cartridge, it may become dislodged from the deck during this procedure. Additionally, there is risk that a user (e.g., a surgeon or surgeon's assistant) may mistake the adjunct as a protective device which needs to be removed prior to the procedure. Therefore, an additional mechanical fixation of the adjunct to the deck of the stable cartridge may be desirable to prevent dislodging from the deck or removal of the adjunct from the deck by a user. As described herein, a suture may be used to further secure the adjunct to the deck of the staple cartridge.

In some examples, the adjunct is adhered to the cartridge deck with an attachment material, which needs to be sticky or tacky enough to keep the adjunct adhered to the deck, but not so sticky that it is difficult to detach from the deck after the stapling procedure is completed. In some examples, a means of mechanically attaching the adjunct to the cartridge deck is provided to further prevent premature removal of the adjunct from the cartridge deck.

FIG. 1A is a side-view schematic of staple cartridge 100 being loaded into a surgical instrument, i.e., surgical instrument 200, according to some examples. Staple cartridge 100 may be loaded into end effector 202 before being positioned at the treatment site. The staple cartridge 100 may be inserted into first jaw frame 204. Anvil 210 may clamp down toward staple cartridge 100 during the stapling procedure. Once the tissue is stapled, anvil 210 may open to leave the staples and adjunct attached to the tissue. Staple cartridge 100 may remain in the first jaw frame 204 as surgical instrument 200 is removed from the treatment site.

With reference to FIG. 1B, implantable adjunct 300 can account for differing tissue thickness by providing support for the thinner sections of tissue. Where the tissue is thick, implantable adjunct 300 can be compressed all the way down since no additional thickness is needed to account for the staple length. Where the tissue is thin, the implantable adjunct 300 is not as compressed, meaning the adjunct provides the additional thickness needed to account for the staple length, thereby providing proper compression in that section of the tissue. FIG. 1B is a schematic showing the implantable adjunct 300 stapled to tissue (T) having different thickness. The individual staples 120*a,b,c,d* have the same height (H), so the implantable adjunct 300 fills in the space for thinner sections of tissue (i.e., the tissue (T) shown at staples 120*b* and 120*d*). For thicker sections of tissue (i.e., the tissue (T) shown at staples 120*a* and 120*c*), the implantable adjunct 300 is more compressed as the staples do not need the additional space (i.e., height) filled in by the implantable adjunct 300.

Figures 1C, 1D:
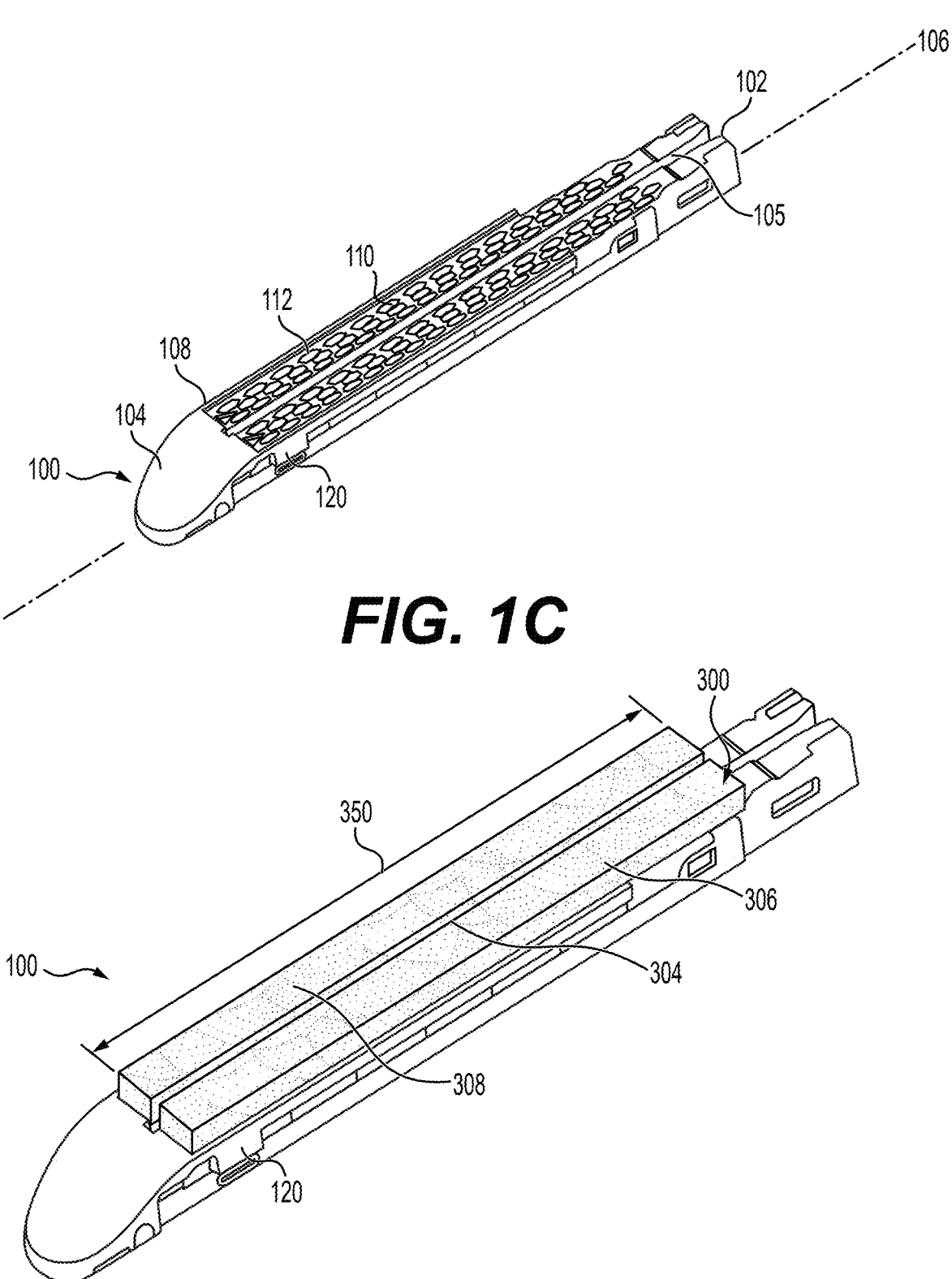
FIG. 1C is a perspective view of a replaceable staple cartridge without an adjunct, according to aspects of the present disclosure.
FIG. 1D is a perspective view of an example staple cartridge and implantable adjunct, according to aspects of the present disclosure.
Figure 1E:
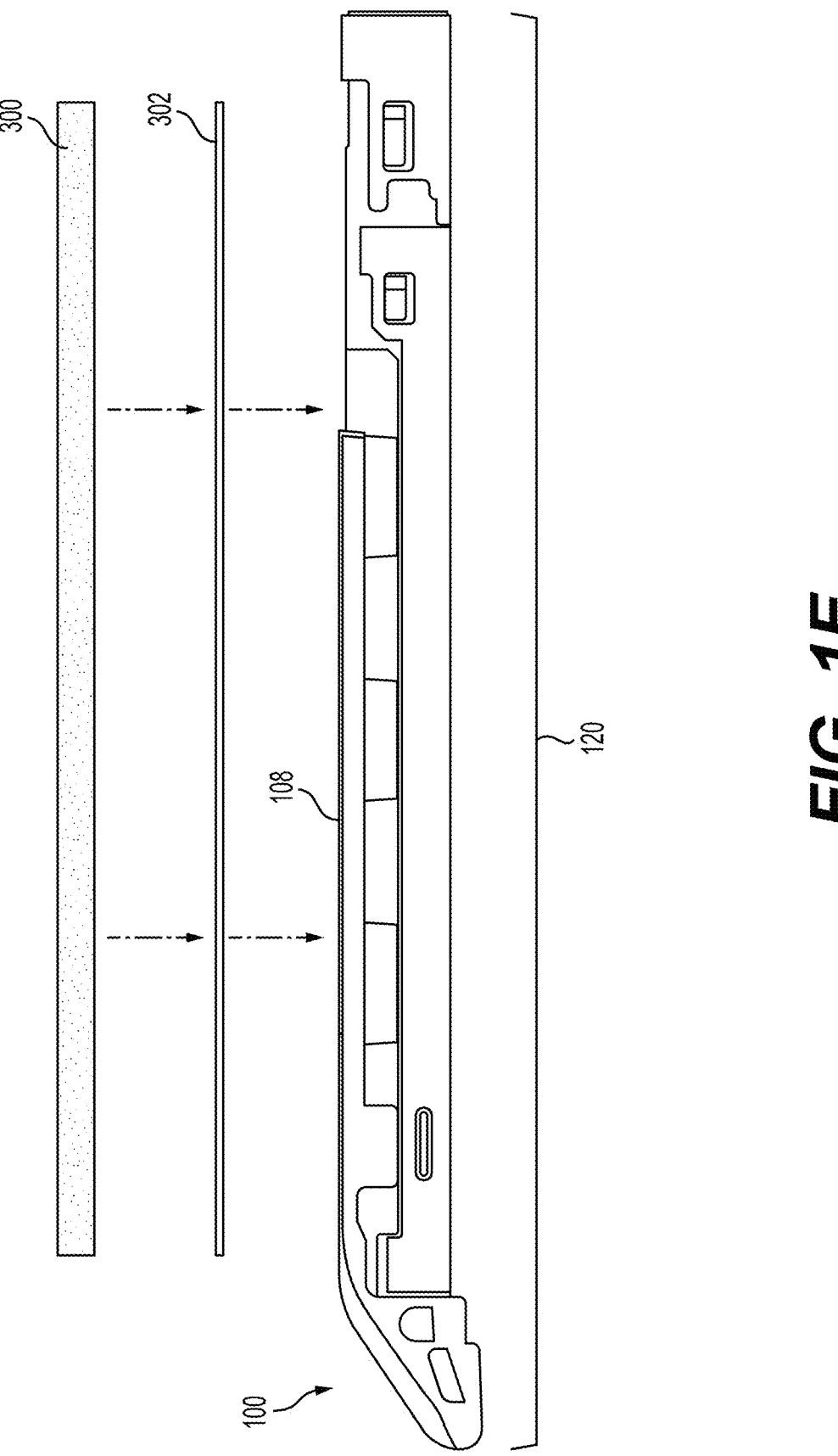
FIG. 1E is a schematic showing the replaceable staple cartridge, mesh layer, and implantable adjunct, according to aspects of the present disclosure.

FIGS. 1C-1E illustrate staple cartridges, according to some examples. FIG. 1C depicts a staple cartridge 100 that does not include an implantable adjunct on deck 108 thereof, according to some examples. In some examples, a staple cartridge 100 comprises an elongate body 120. The elongate body 120 may comprise a longitudinal slot 105 extending along a longitudinal axis 106 from a proximal end 102 toward a distal end 104 of the elongate body 120. In some examples, the elongate body comprises a deck 108, and a plurality of staple pockets 110. Each of the staple pockets 110 may be accessible via an opening 112 in the deck 108.

FIG. 1D depicts an implantable adjunct 300 adhered to the deck of the staple cartridge 100. Adjunct 300 can be adhered to staple cartridge 100 with an attachment material. As described above, the attachment material can provide sufficient adhesion for adjunct 300 to remain adhered to deck 108 when being positioned at the treatment site, but the adhesion does not impair the ability of adjunct 300 from being detached from deck 108 when being implanted. In some instances, attachment material can be an adhesive, adhesive strip, double-sided tape.

For background, the staples of the systems described herein are fired through adjunct 300 during the stapling procedure. In some instances, adjunct 300 can include longitudinal groove 304 within length 350 of the adjunct and aligned with the longitudinal slot of the staple cartridge 100. Longitudinal groove 304 provides a path for a knife (not shown in figures) to traverse such that the knife does not need to cut through adjunct 300, thereby preserving the edge on the knife. When adjunct 300 includes sled groove 304, adjunct 300 can be considered to be separated into adjunct first side 306 and adjunct second side 308. As will be appreciated, surgical instruments 200 such as a surgical stapler can have both a stapling function and a cutting function. As such, a knife can be included to make the incision along the tissue, as well as making a cut through mesh layers (e.g., mesh layer 302 discussed below). Various implementations of a knife within a surgical instrument will be appreciated by a person of skill, but as a non-limiting example, the publication U.S. Patent Pub. No. 2024/0108333 provides an exemplary knife (see e.g., FIG. 5, showing a knife portion 1920 with a tissue cutting edge 1922). U.S. Patent Pub. No. 2024/0108333 is herein incorporated by reference in its entirety as if fully set forth below.

As depicted in FIG. 1E, in some examples, adjunct 300 can include laminated layers, such as a foam and/or porous material laminated with a mesh material. In some examples, adjunct 300 can include a film layer and/or a mesh layer 302. The film layer can comprise material commonly used with absorbable monofilament sutures and can be heat processed with a mesh layer to act as a bonding agent to hold the mesh and foam of the adjunct 300 together. In some examples, the longitudinal groove 304 is disposed in the foam and/or porous material but the mesh material 302 remains intact. In some examples, the mesh layer 302 is perforated along the longitudinal groove to provide a path for a knife (not shown in figures) to traverse, thereby facilitating cutting of the mesh 302 and preserving the edge on the knife.

As discussed above, a suture may provide a means of mechanically fixing the adjunct 300 to the deck 108 of the staple cartridge 100 to further prevent premature removal of the adjunct 300 from the cartridge deck 108. In some examples, as described herein, a suture is provided within a longitudinal groove 304 of the implantable adjunct 300 secured at each of the proximal end 102 and distal end 104 of the elongate body 120 of the staple cartridge. In some examples, the adjunct comprises a mesh layer 302 and the suture rests within the longitudinal groove 304 and on top of the mesh layer 302. In some examples, when a knife is passed through the longitudinal slot of the staple cartridge 100, the mesh layer 302 is cut and the adjunct 300 can be detached from the deck 108 of the cartridge 100 while the suture remains attached to the cartridge. In some examples, the suture is biased to one side of the longitudinal slot 105 of the cartridge 100 to prevent the suture from being cut or severed when a knife is passed through the longitudinal slot 105 of the staple cartridge 100. While some examples disclosed herein depict two sutures or two portions of a suture provided along the longitudinal slot 105, it will be appreciated that only one suture may be provided along the longitudinal slot to provide additional room for a knife to pass through the longitudinal slot 105 without cutting the suture.

Figure 2A:
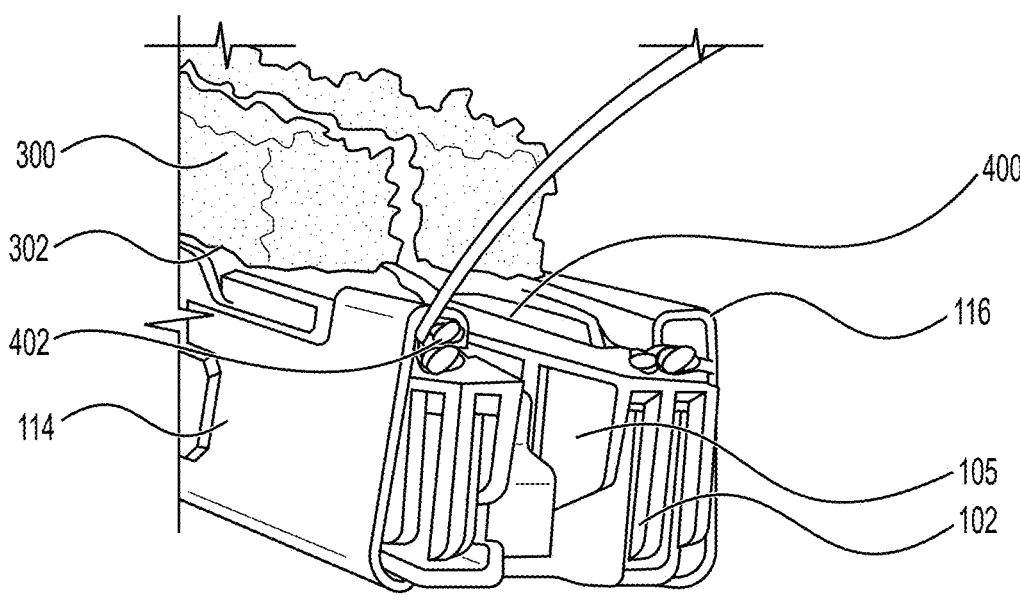
FIG. 2A is a perspective view of a proximal end of an example staple cartridge with a cartridge pan configured to secure a suture, according to aspects of the present disclosure.

FIGS. 2A-2E depict a proximal end 102 of a staple cartridge configured to secure at least one suture. In some examples, the staple cartridge further comprises a pan 114. The pan 114 may provide further support for the elongate body 120 of the staple cartridge. In some examples, a portion of the pan 114, at the proximal end 102 of the cartridge, comprises hooks 116 for securing at least one suture 400 at the proximal end 102 of the staple cartridge. As depicted in FIG. 2A, the ends 402 of a suture 400 may be knotted, and hooks 116 may be sized such that the knotted end 402 of the suture is retained by the hooks 116. In some examples, the hooks 116 are crimped metal. The hooks 116 may be approximately .050" long.

Figure 2B:
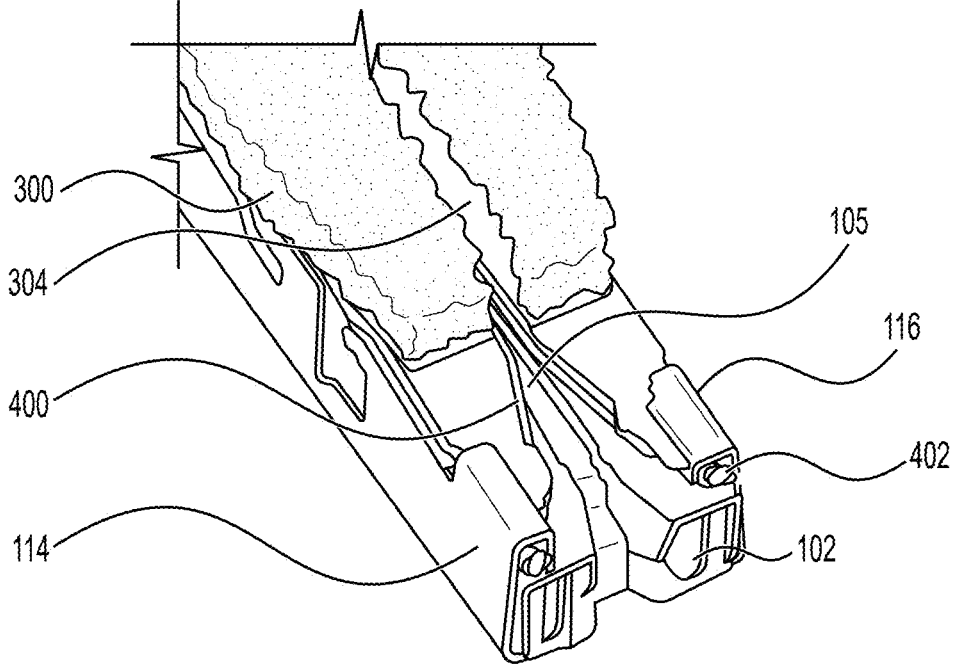
FIG. 2B is a perspective view of a proximal end of the staple cartridge with a cartridge pan configured to secure a suture, according to aspects of the present disclosure.
Figure 2C:
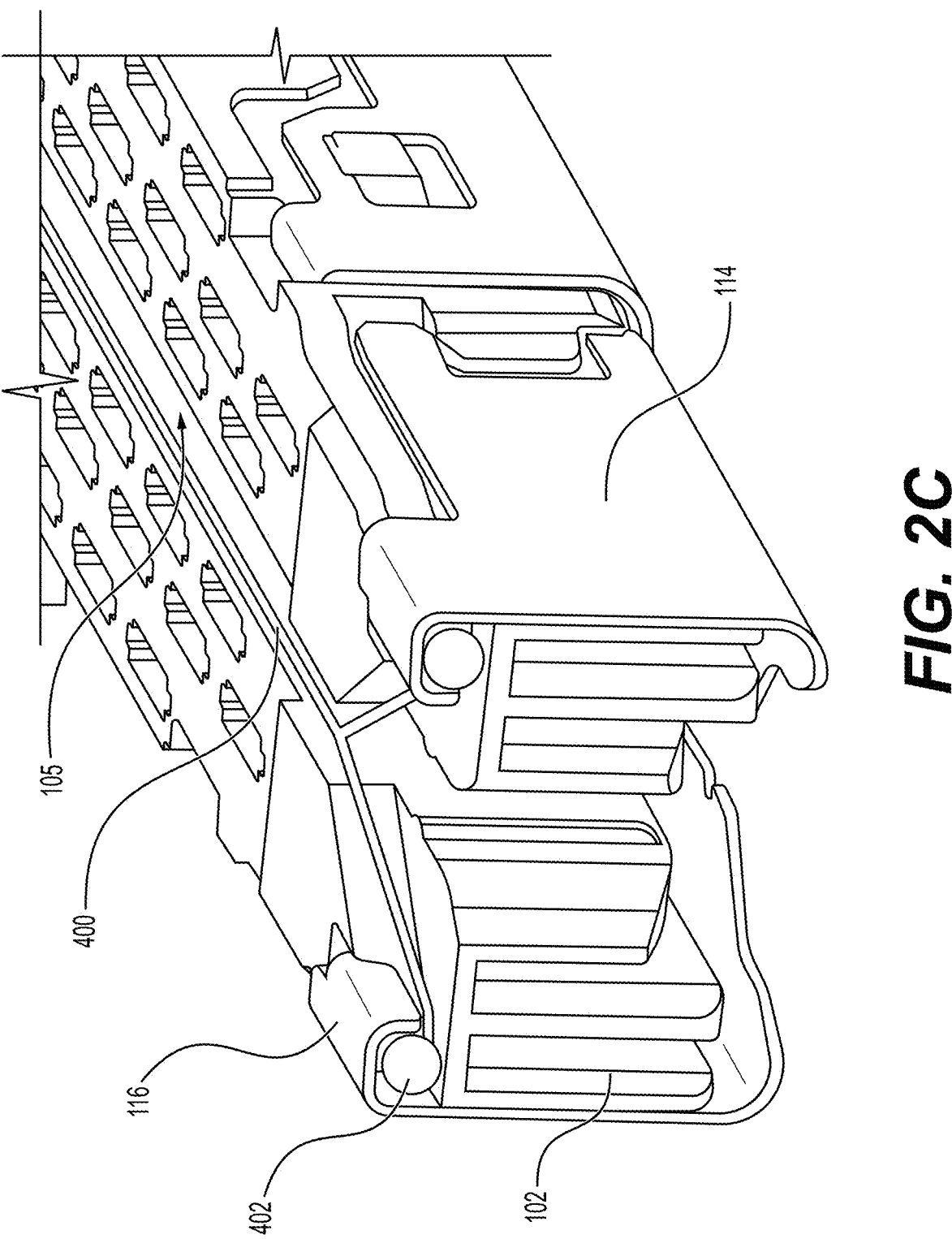
FIG. 2C is a perspective view of a proximal end of the staple cartridge with a cartridge pan configured to secure a suture, according to aspects of the present disclosure.
Figure 2D:
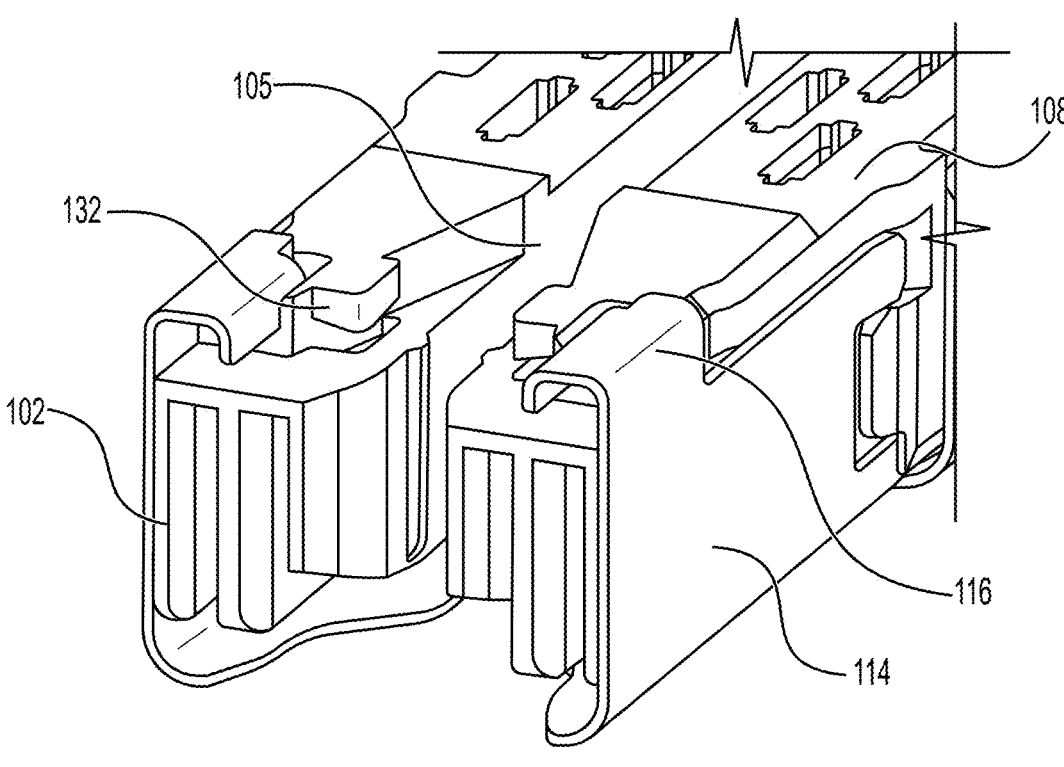
FIG. 2D is a perspective view of a proximal end of the staple cartridge with a cartridge pan configured to secure a suture, according to aspects of the present disclosure.
Figure 2E:
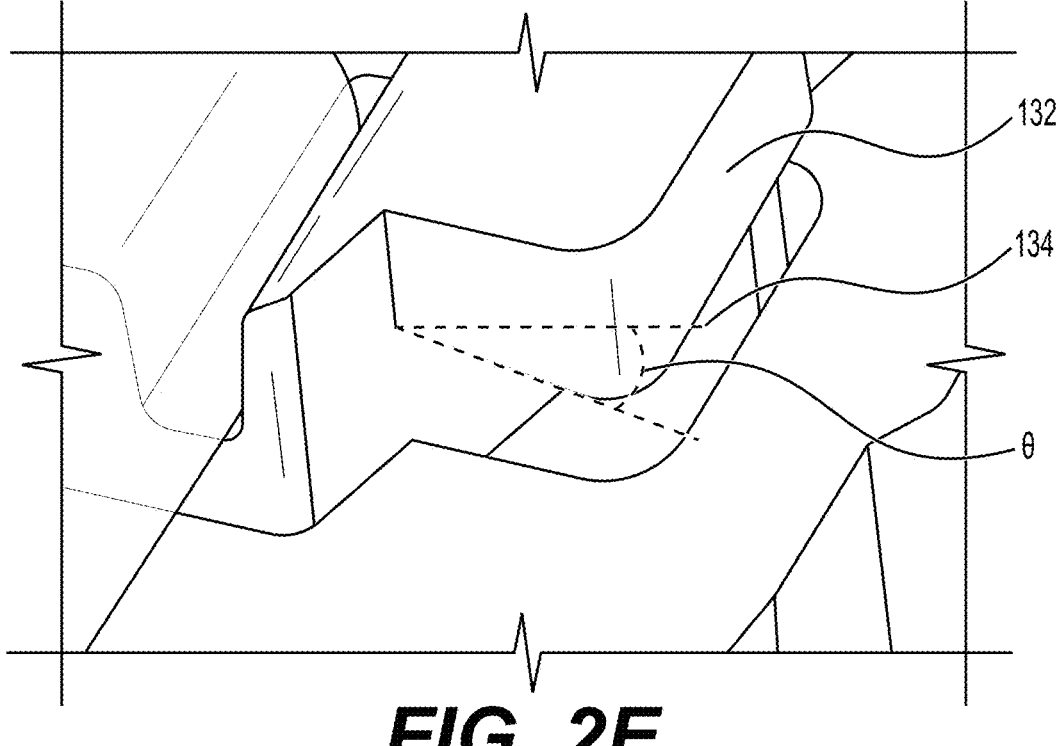
FIG. 2E is a detailed view a suture hook formed at the proximal end of the example staple cartridge shown in FIG. 2D, according to aspects of the present disclosure.

As depicted in FIGS. 2A and 2B, two sutures 400 or two ends of a single suture may be provided through the longitudinal groove 304 of the implantable adjunct 300, according to some examples. The hooks 116, may bias each of the two sutures or two ends of a single suture toward the outside of the longitudinal slot 105 of the staple cartridge 100 to provide a space for a knife to pass between when passing though the longitudinal slot 105 during a cutting operation. As discussed above, the adjunct 300 may comprise a mesh 302 which the sutures rest on to tension the adjunct down onto the deck of the cartridge. As contemplated above, a single suture or single portion of a suture may be provided through the longitudinal grove groove 304 of the implantable adjunct 300, as opposed to two sutures or two portions of a suture. The other end or ends of the suture 400 may be secured to the distal end of the cartridge, as discussed herein. Alternatively, as depicted in FIG. 2C, a Y-shaped suture, or two sutures with an intertwined middle portion, may be utilized with a single strand running through the longitudinal groove (not shown) of the implantable adjunct.

As depicted in FIGS. 2A, 2B, 2D, and 2E, the proximal end 102 of the elongate body may further comprise a suture guide 132 directing the at least one suture 400 into the longitudinal groove 304 of the implantable adjunct 300. In some examples, the suture guides 132 comprises a bottom surface 134 angled relative to the deck 108 at an angle θ (see FIG. 2E). In some examples, the bottom surface 134 is angled relative to the deck 108 at an angle θ of approximately 0 degrees to approximately 20 degrees. In some examples, the downward angle of the suture guides 132 positions the sutures below the deck 108, such that the sutures maintain a downward tension on the adjunct 300 towards the deck 108.

Figure 3:
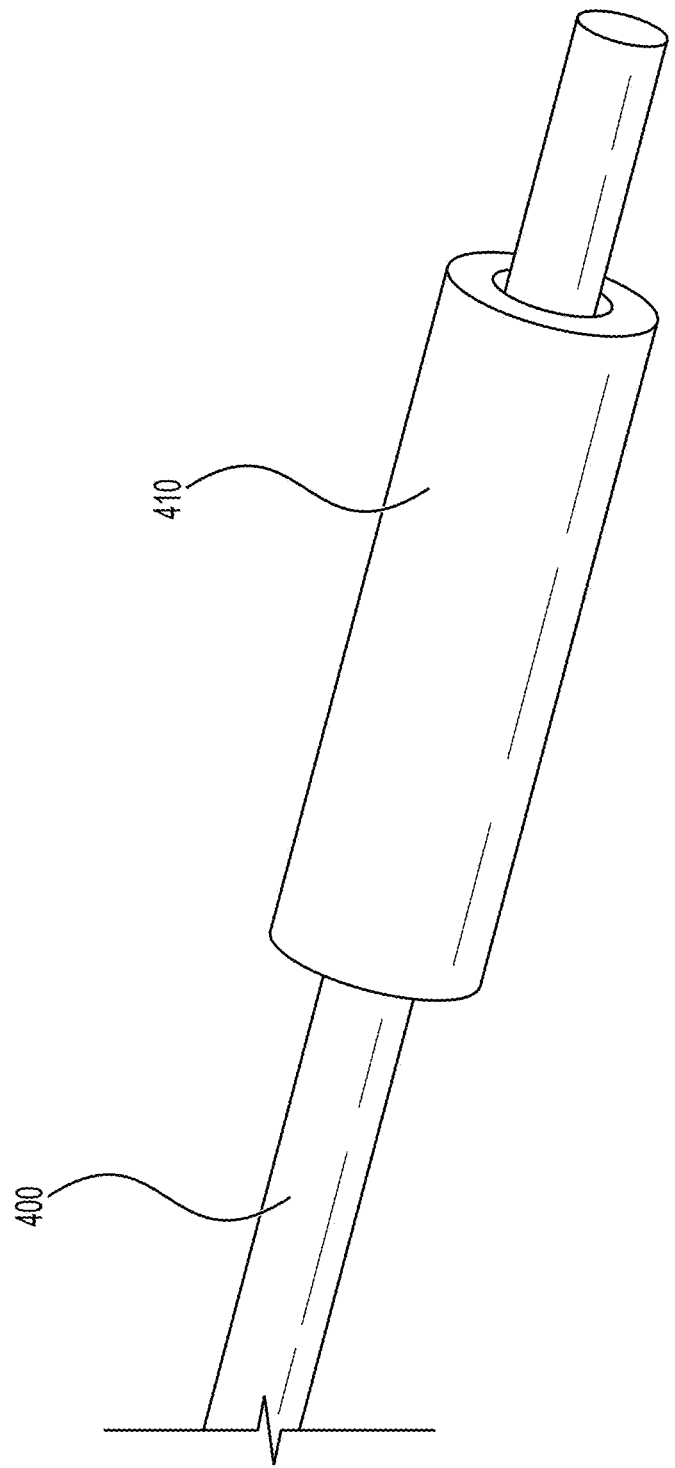
FIG. 3 is a perspective view of a sleeve coupled to a suture, according to aspects of the present disclosure.

With reference to FIG. 3, in some examples, a suture 400 comprises a sleeve 410 attached to at least one end of the suture 400. The sleeve 410 may comprise a metal or another suitable material which can be crimped onto the suture 400. The sleeve 410 can provide a feature for securing the suture to a portion of the elongate body 120 of the cartridge 100. FIGS. 4A-6B depict a proximal end 102 of an elongate body 120 of a staple cartridge having recesses 144 to retain a sleeve 410 attached to an end of a suture 400.

Figure 4A:
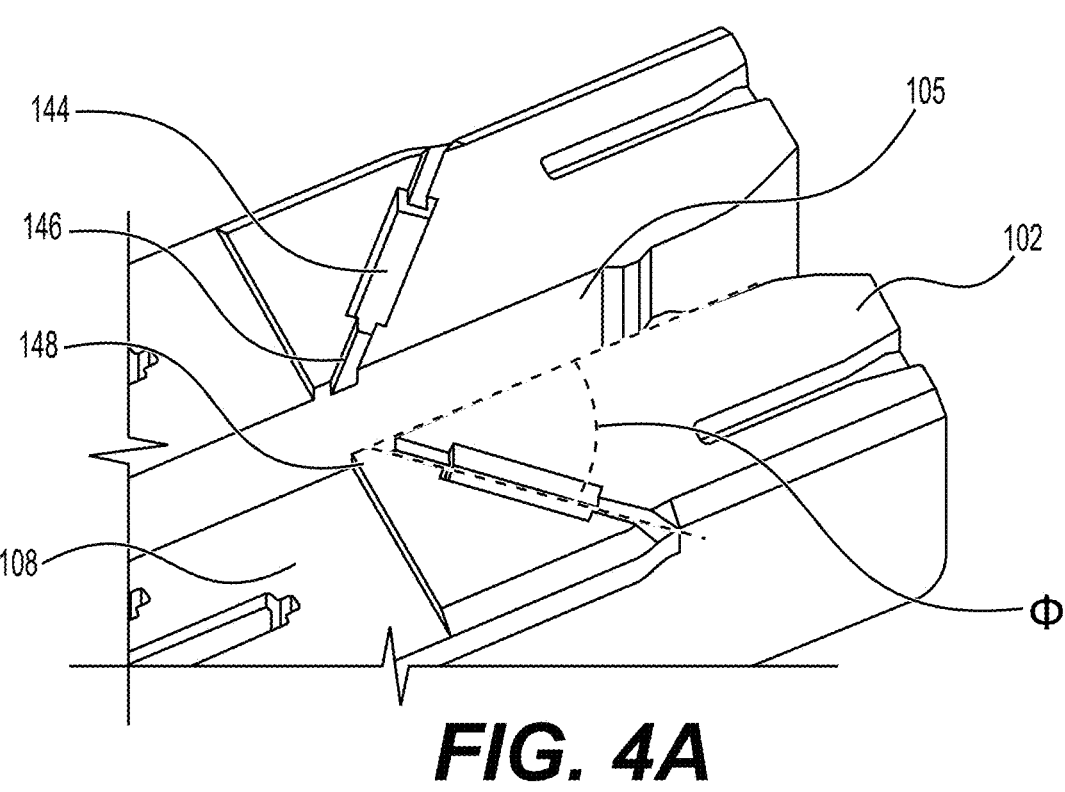
FIG. 4A is a top perspective view of a proximal end of an example staple cartridge, according to aspects of the present disclosure.
Figure 4B:
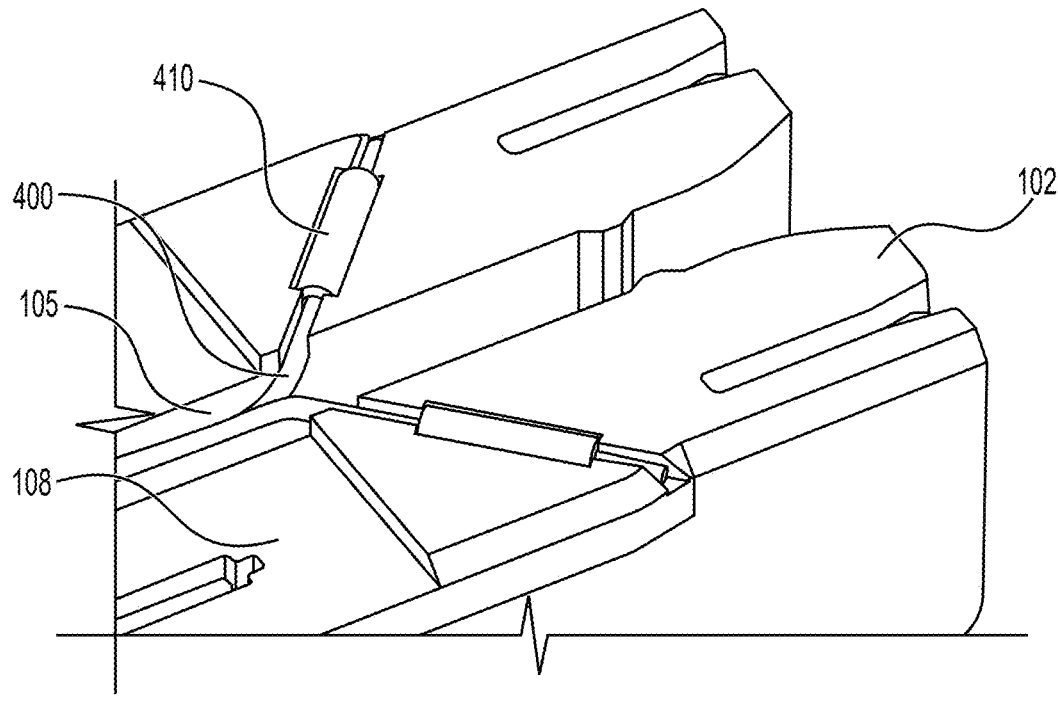
FIG. 4B is a top perspective view of a proximal end of the example staple cartridge shown in FIG. 4A with a suture coupled thereto, according to aspects of the present disclosure.

FIGS. 4A and 4B, depict a recess 144 provided in a top surface of the distal end 102 of the elongate body of the staple cartridge. In some examples, the recess 144 is sized to form a press-fit or an interference fit with the sleeve 410. In some examples, recess 144 is provided at an angle @ relative to a length of the longitudinal slot 105 (i.e., angle relative to the longitudinal axis 106, as depicted in FIG. 1C, along which the longitudinal slot 105 is provided). In some examples, the angle @ is approximately 30 to 60 degrees. As depicted in FIG. 4B when sleeve 410 is provided within the recess 144, the suture 400 extends into a suture recess 146 sized to fit the suture (smaller than the recess 144 sized for the sleeve) and around corner 148, such that the suture is biased to one side of the longitudinal slot 105. In some examples, the recess 144 is provided below the deck 108, such that the suture 400 will be positioned to tension the adjunct 300 (not shown in FIGS. 4A and 4B) downward on to the deck when the suture is provided through the longitudinal groove and on top of the mesh layer of the adjunct.

Figure 5A:
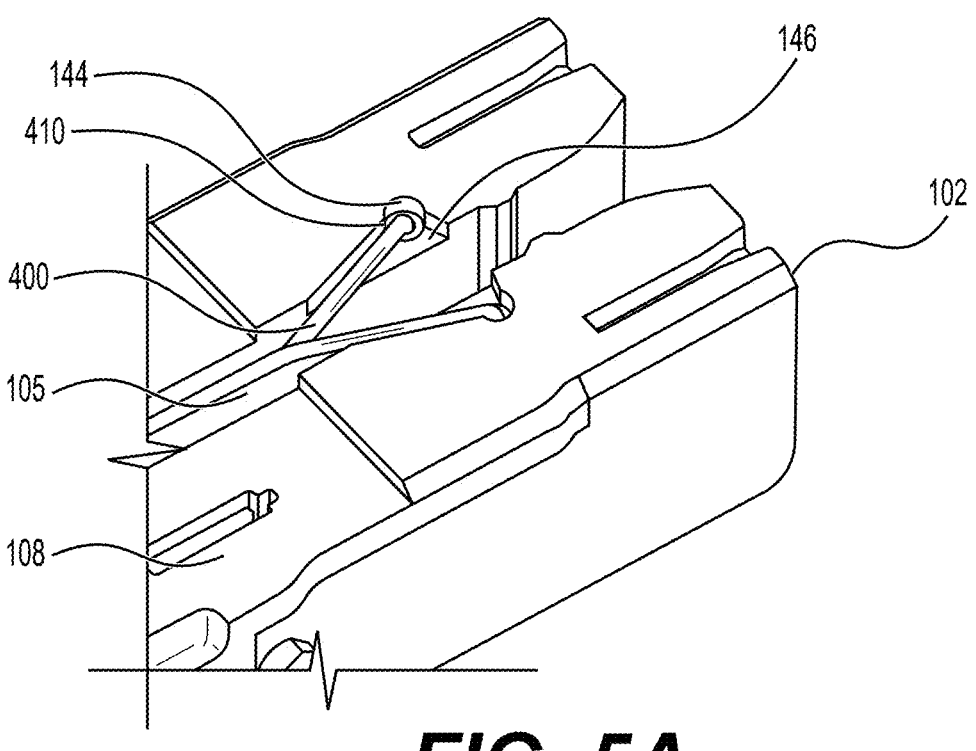
FIG. 5A is a bottom perspective view of a proximal end of an example staple cartridge, according to aspects of the present disclosure.
Figure 5B:
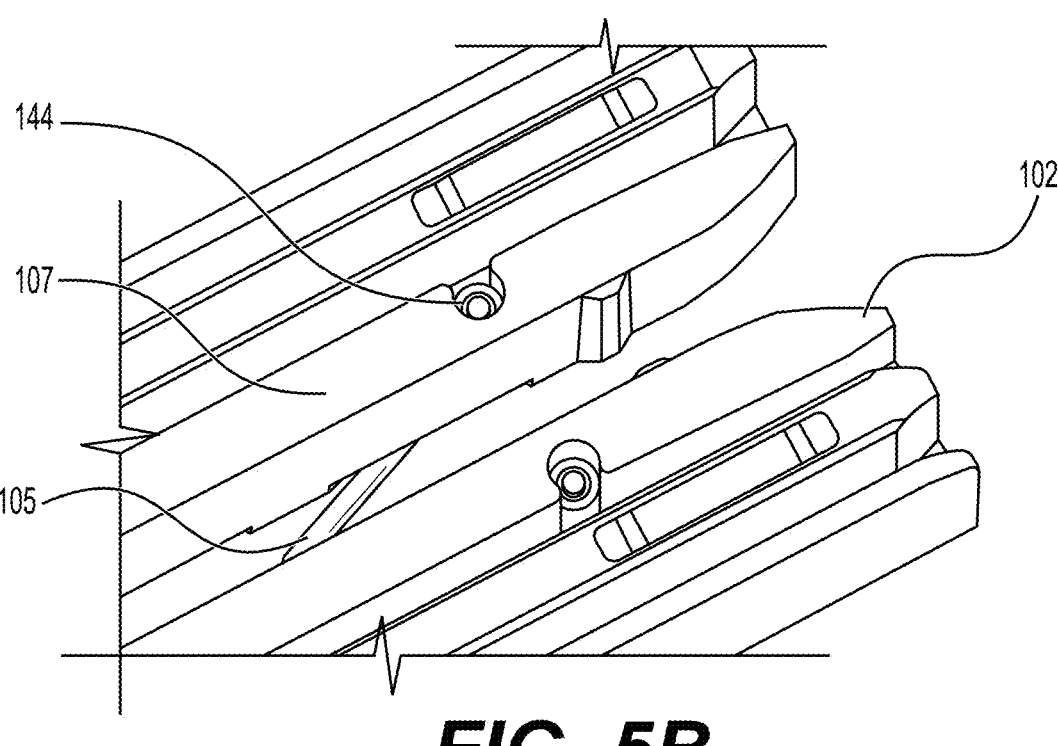
FIG. 5B is a bottom perspective view of the example staple cartridge shown in FIG. 5A, according to aspects of the present disclosure.

FIGS. 5A and 5B, depict a recess 144 provided through top surface of the distal end 102 of the elongate body of the staple cartridge. In some examples, the recess 144 is sized to form a press-fit with the sleeve 410. In some examples, recess 144 is provided orthogonal to a length of the longitudinal slot 105, extending from the top surface of the elongate body toward a bottom surface of the elongate body. As depicted in FIG. 5B when sleeve 410 is provided within the recess 144, the suture 400 extends into a suture recess 146, such that the suture is biased to one side of the longitudinal slot 105. In some examples, the bottom surface of the suture recess 146 is provided below the deck 108, such that the suture 400 will tension the adjunct (not shown in FIGS. 5A and 5B) downward on to the deck when the suture is provided through the longitudinal groove and on top of the mesh layer of the adjunct.

Figure 6A:
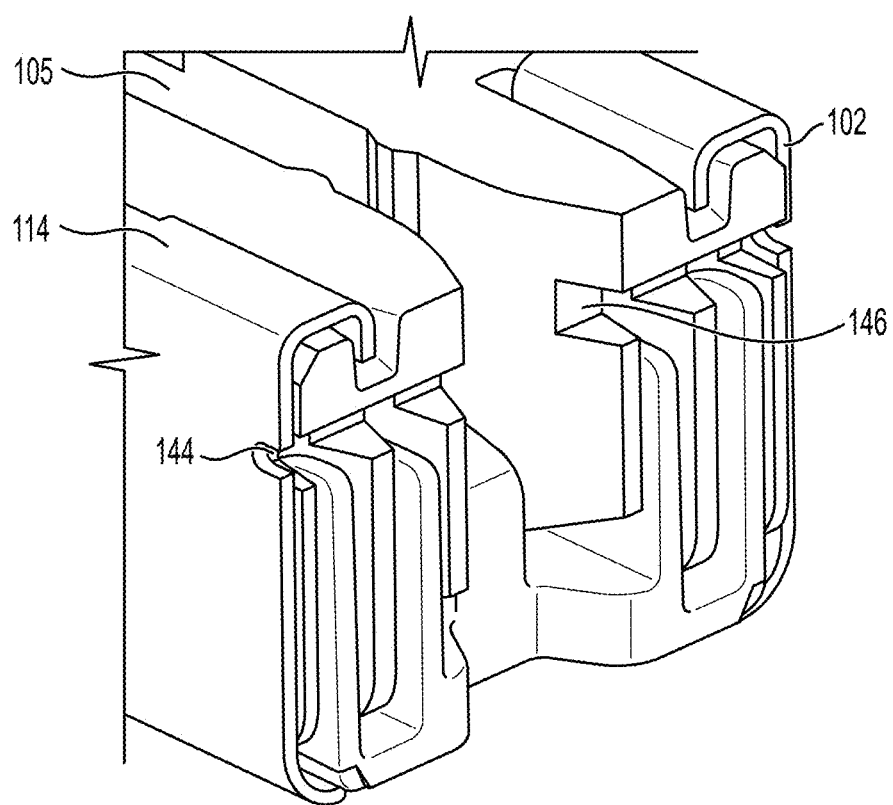
FIG. 6A is a perspective view of a proximal end of an example staple cartridge configured to secure a suture, according to aspects of the present disclosure.
Figure 6B:
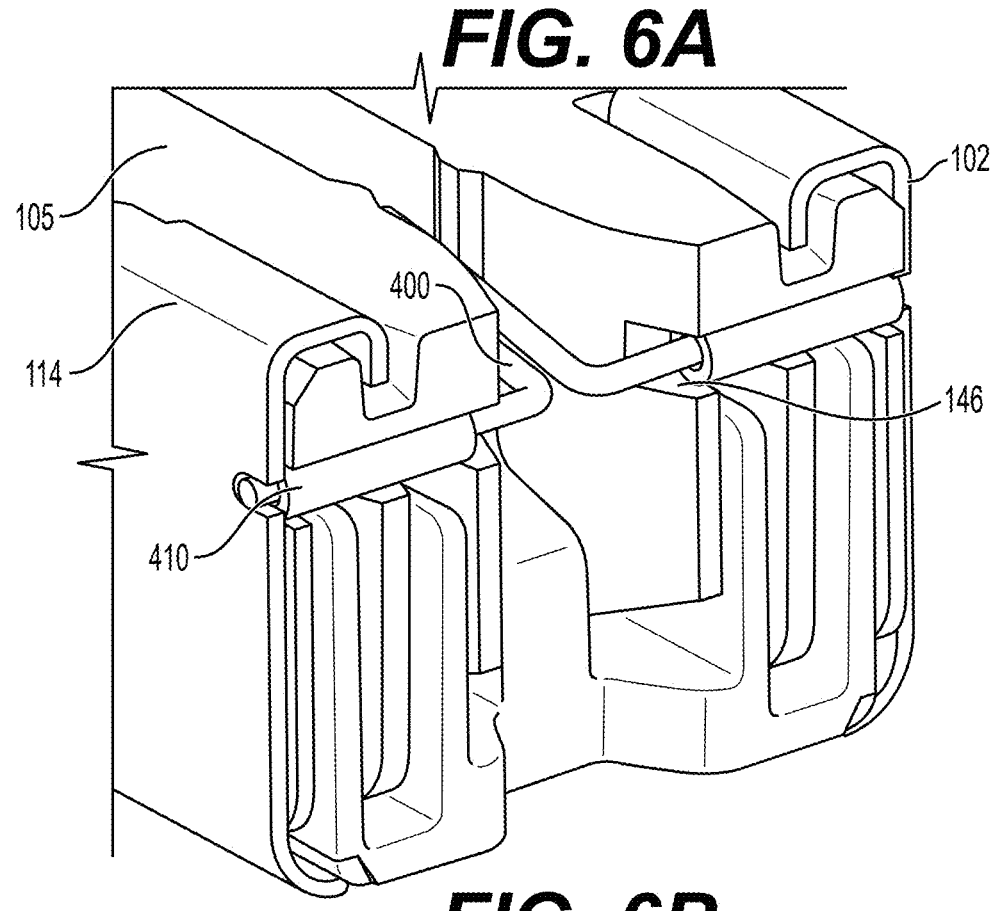
FIG. 6B is a perspective view of the example staple cartridge shown in FIG. 6A with a suture coupled thereto, according to aspects of the present disclosure.

FIGS. 6A and 6B, depict a recess 144 provided at the proximal end 102 of the elongate body of the staple cartridge. In some examples, the recess 144 is sized to form an interference or press-fit with the sleeve 410. In some examples, recess 144 is provided perpendicular to a length of the longitudinal slot 105, extending across the proximal end 102 of the elongate body. As depicted in FIG. 6B when sleeve 410 is provided within the recess 144, the suture 400 extends into a suture recess 146, such that the suture is biased to one side of the longitudinal slot 105. In some examples, the recess 144 is provided below the deck 108, such that the suture 400 will tension the adjunct (not shown in FIGS. 6A and 6B) downward on to the deck when the suture is provided through the longitudinal groove and on top of the mesh layer of the adjunct.

Figure 7A:
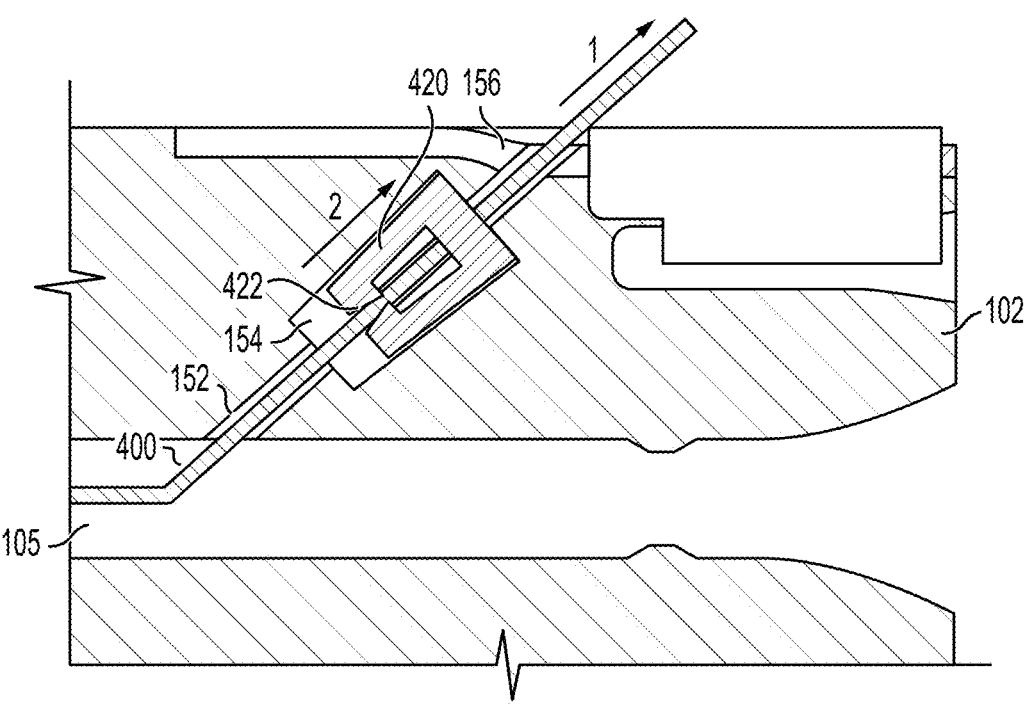
FIG. 7A is a cross-sectional schematic of a proximal end of an example staple cartridge configured to secure a suture, according to aspects of the present disclosure.
Figure 7B:
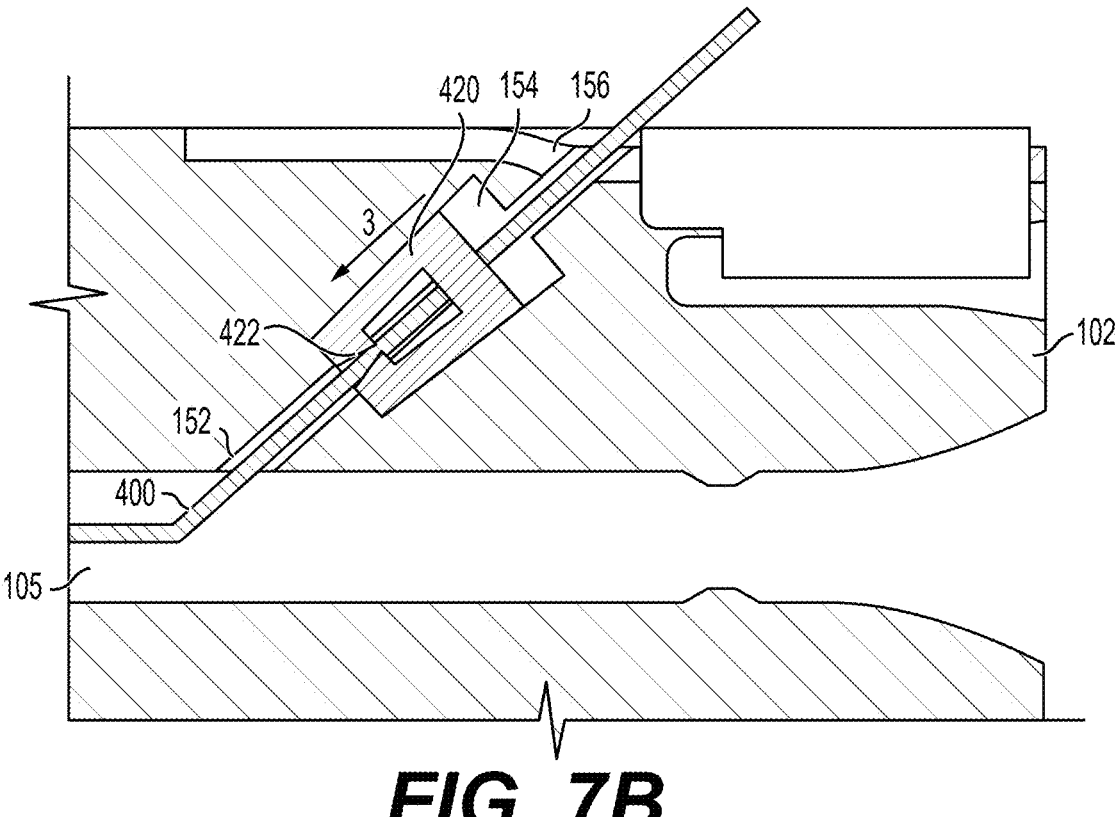
FIG. 7B is a cross-sectional schematic of a proximal end of an example staple cartridge configured to secure a suture, according to aspects of the present disclosure.

With references to FIGS. 7A and 7B, the proximal end 102 of the elongate body 120 comprises a cavity 154 to receive a collet 420, according to some examples. The collet 420 may comprise a first opening 422 to receive the at least one suture 400 therethrough allowing the suture to be pulled through (in direction 1) when the collet 420 is moved away from the longitudinal slot (in direction 2). In some examples, the cavity 154 tapers inward toward the longitudinal slot 105 such that the first opening 422 of the collet 420 clamps onto the at least one suture 400 as the collet 420 moves toward the longitudinal slot 105 (in the direction 3) under tension of the suture and restricts the suture 400 from sliding back through the first opening 422, thereby providing a self-tensioning mechanism. The suture 400 may enter the cavity through a first aperture 152 from the longitudinal slot 105 and exit through a second aperture 156 to an outer surface of the elongate body. The first aperture 152 may be angle relative to the longitudinal slot such that the suture is biased to one side of the longitudinal slot 105. In some examples, the first aperture 152 is provided below the deck such that the suture 400 will tension the adjunct (not shown in FIGS. 7A and 7B) downward on to the deck when the suture is provided through the longitudinal groove and on top of the mesh layer of the adjunct.

FIGS. 8A-10B depict a distal end 102 of an elongate body 120 of a staple cartridge configured to secure a suture 400.

Figure 8A:
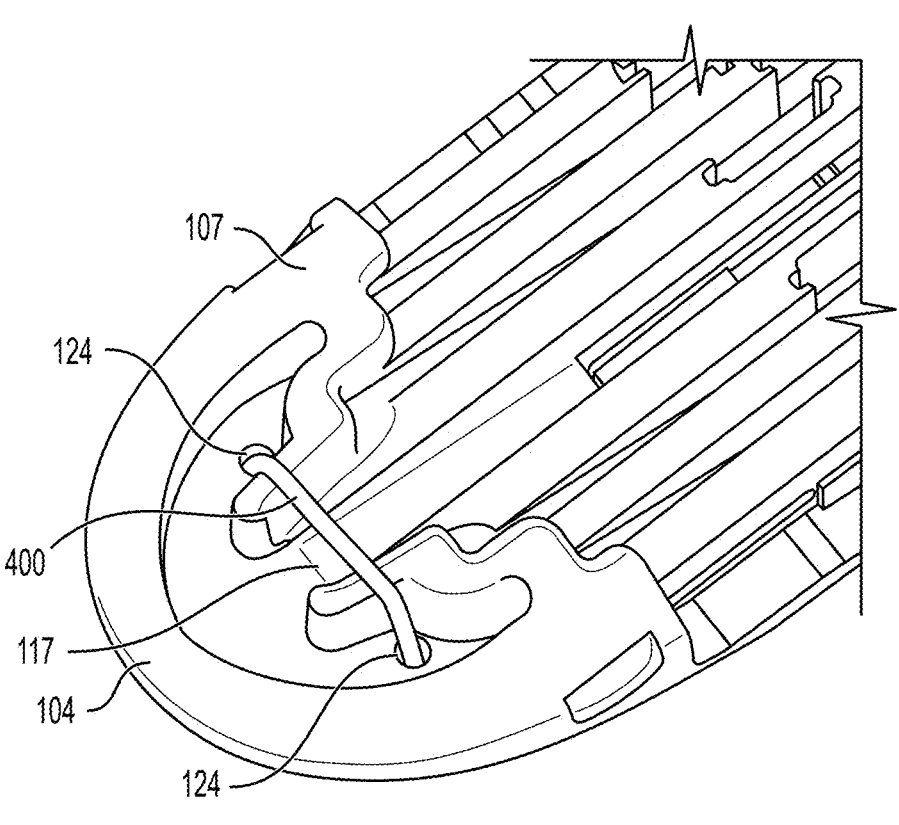
FIG. 8A is a bottom perspective view of a distal end of an example staple cartridge with a suture coupled thereto, according to aspects of the present disclosure.
Figure 9A:
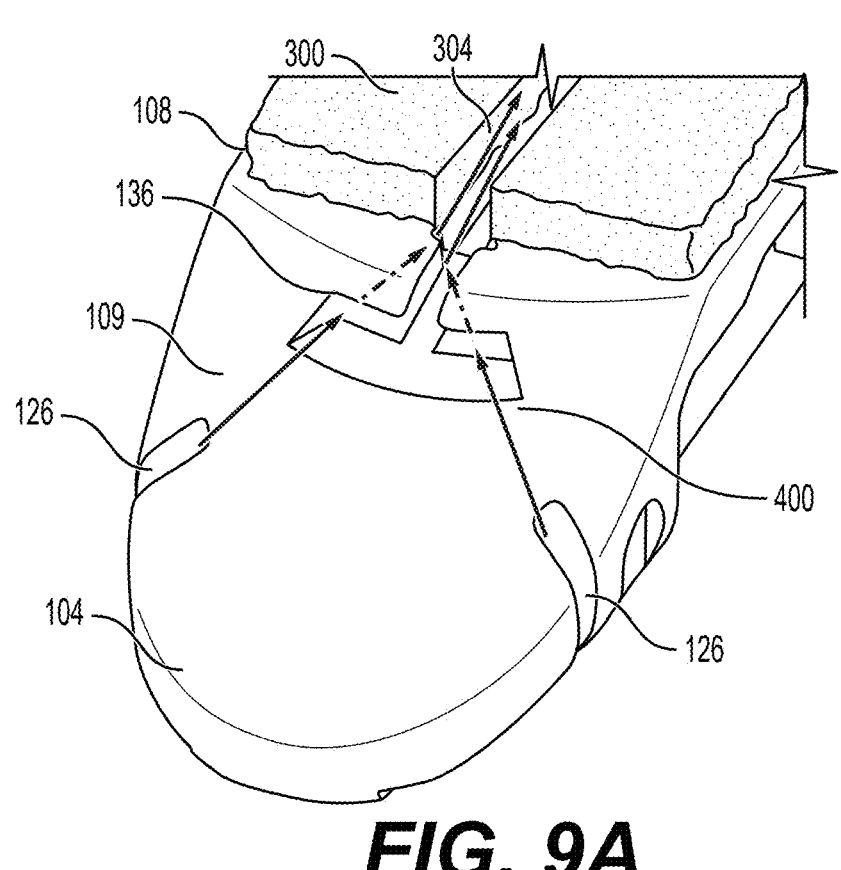
FIG. 9A is a top perspective view of a distal end of an example staple cartridge with a suture coupled thereto, according to aspects of the present disclosure.
Figure 9B:
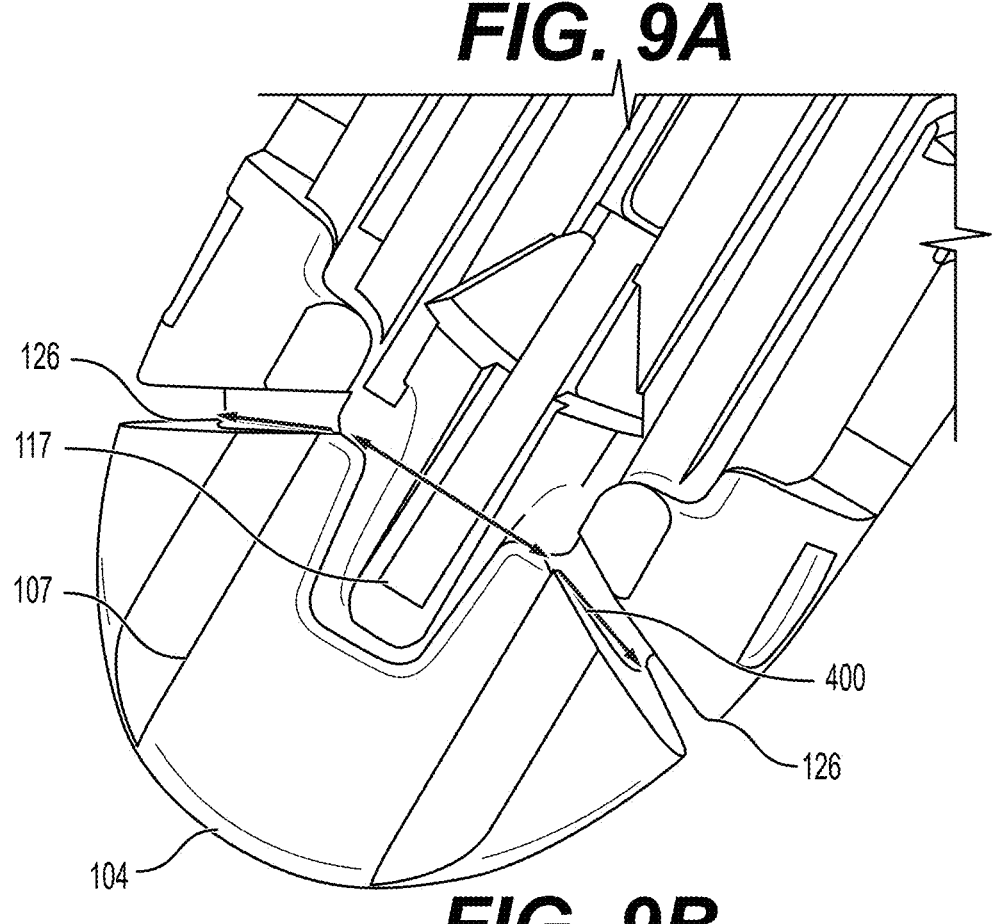
FIG. 9B is a bottom perspective view of the example staple cartridge shown in FIG. 9A, according to aspects of the present disclosure.
Figure 10A:
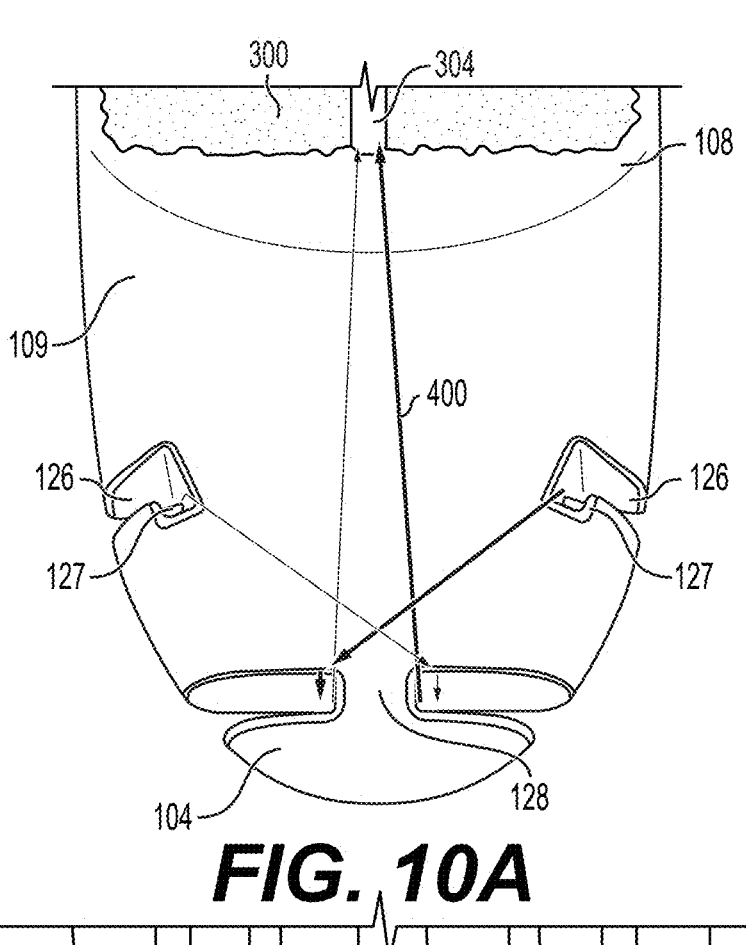
FIG. 10A is a top plan view of a distal end of an example staple cartridge with a suture coupled thereto, according to aspects of the present disclosure.
Figure 10B:
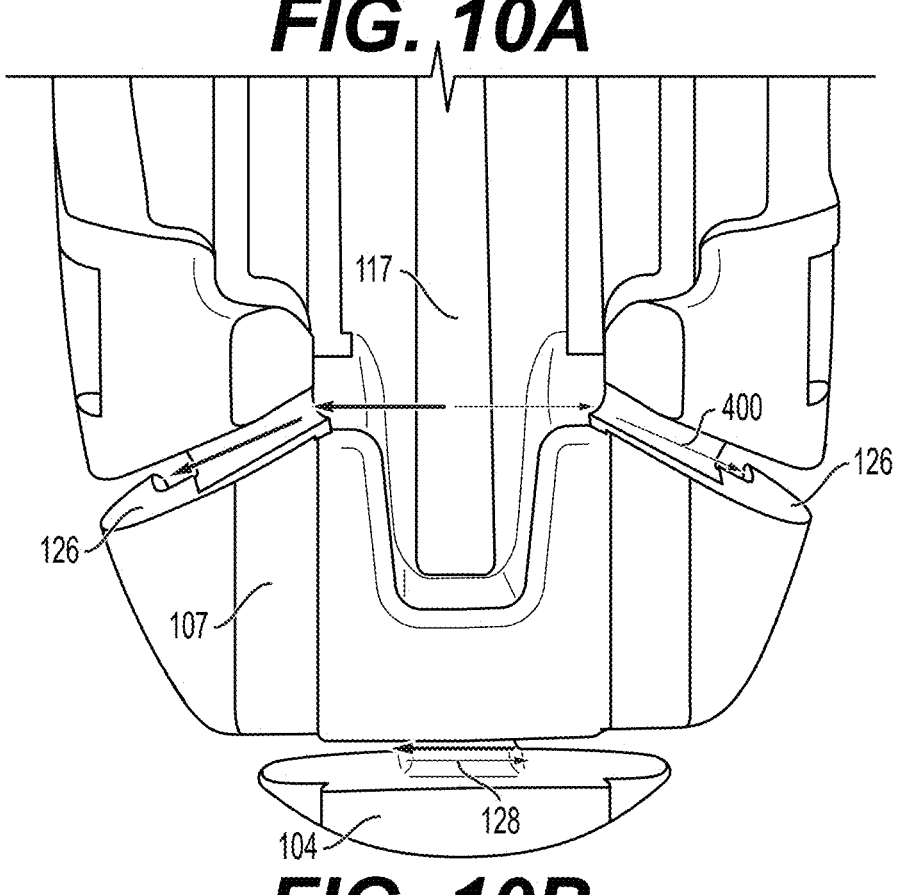
FIG. 10B is a bottom plan view of the example staple cartridge shown in FIG. 10A, according to aspects of the present disclosure.
Figure 11:
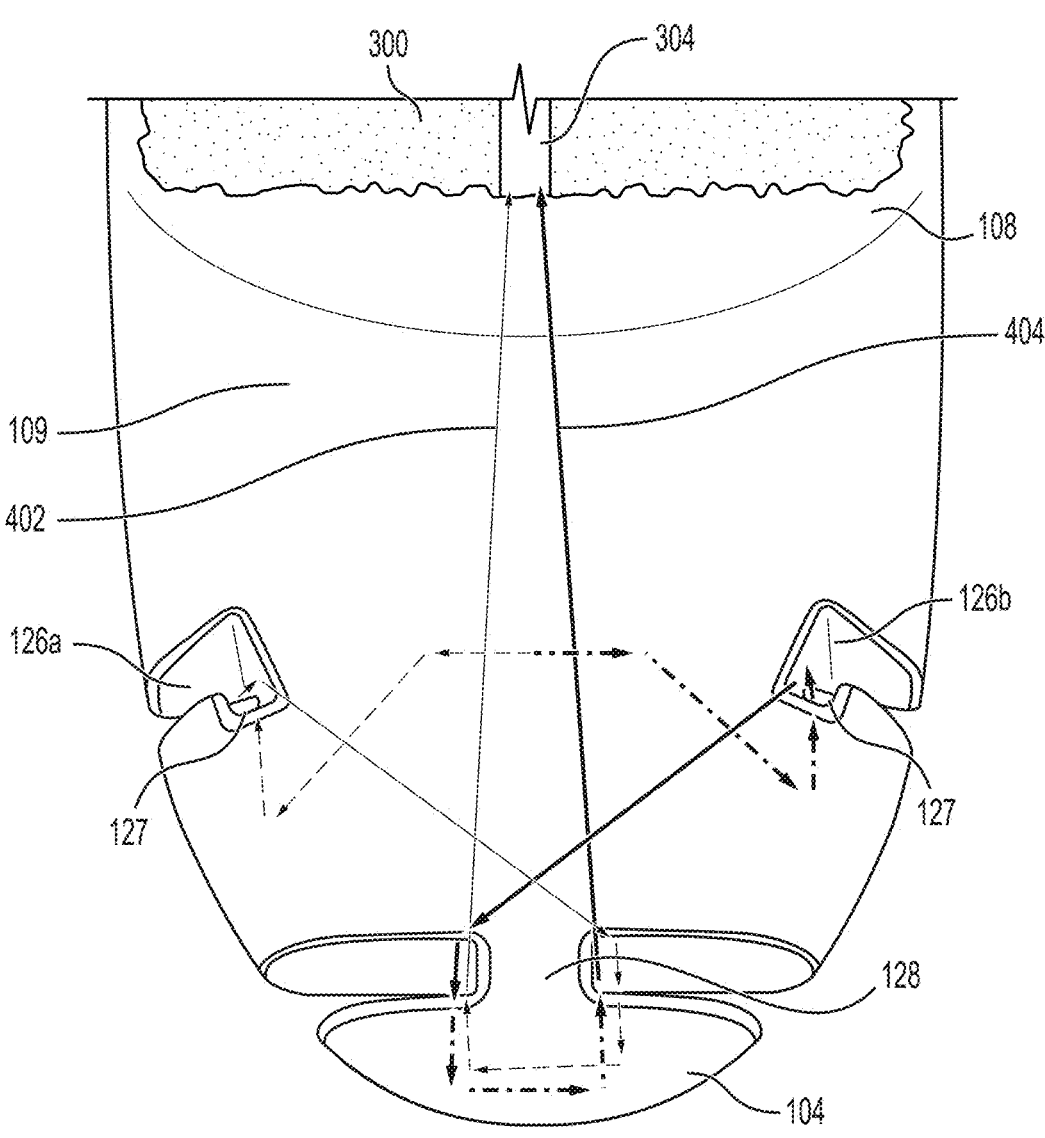
FIG. 11 is a top plan view of a distal end of an example staple cartridge with a suture coupled thereto, according to aspects of the present disclosure.

As depicted in FIGS. 8A, 9B, and 10B, in some examples, the distal end 104 comprises a cutting slot 117 on an underside 107 of the elongate body 120. The cutting slot may be formed by bridging the suture 400 over a portion of the underside of the elongate body thereby forming a space between the underside 107 of the elongate body 120 and the at least one suture 400 to accommodate a cutting instrument. The cutting slot 117 may provide space for a cutting instrument, such as a scalpel or scissors, to cut the suture 400, if needed.

Figure 8B:
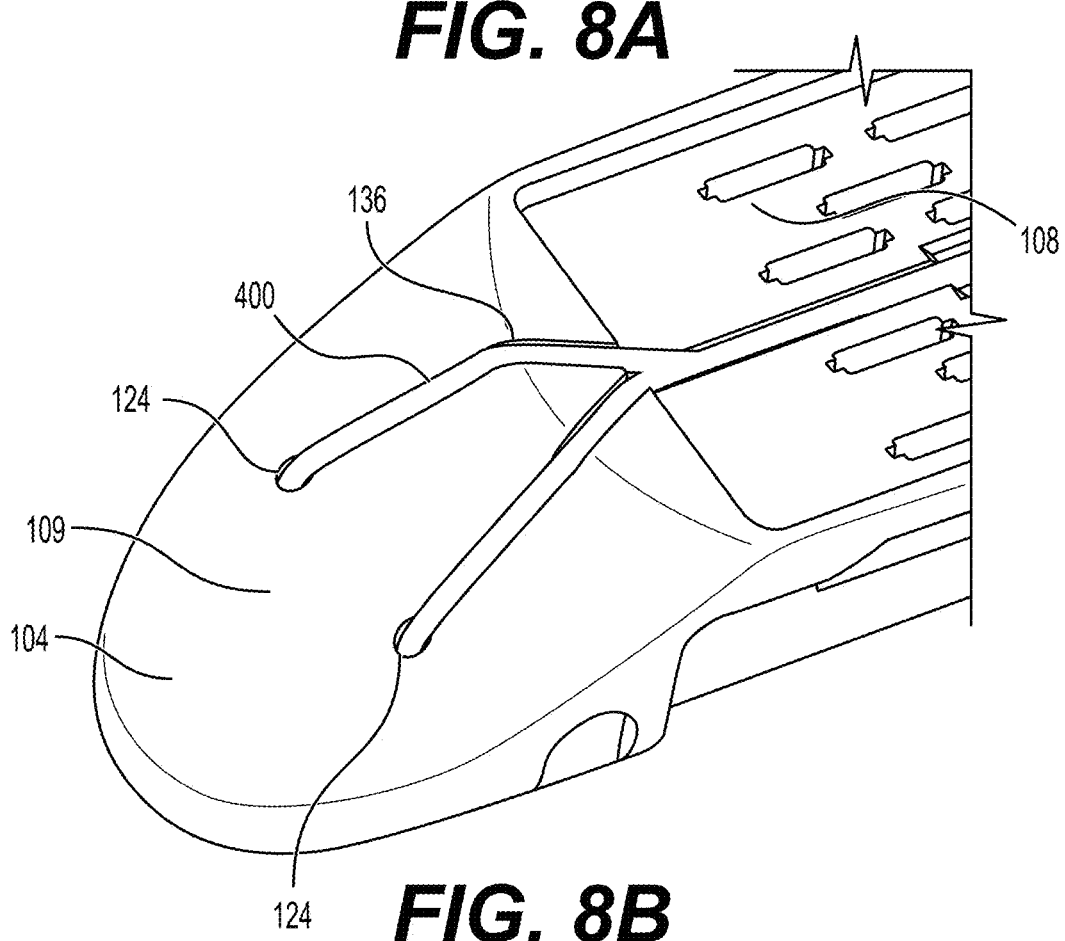
FIG. 8B is a top perspective view of the example staple cartridge shown in FIG. 8A, according to aspects of the present disclosure.

With reference to FIGS. 8A and 8B, in some examples, the distal end 104 of the staple cartridge comprises two through holes 124 extending from a topside 109 to the underside 107 of the elongate body 120. A suture 400 may be looped through the two through holes and across the cutting slot 117 on the underside 107 of the elongate body 120. On the topside 109 of the distal end 104, the two through holes may be provided below the deck 108 such that the suture 400 will tension the adjunct (not shown in FIGS. 8A and 8B) downward on to the deck 108 when the suture is provided through the longitudinal groove and on top of the mesh layer of the adjunct. The distal end 104 may further comprise guide ledges 136 to guide the suture 400 into the longitudinal groove of the adjunct.

With reference to FIGS. 9A and 9B, in some examples, the distal end 104 of the elongate body 120 comprises two side grooves 126. In some examples, the suture 400 is looped around the two side grooves 126 to secure the at least one suture 400 to the distal end 104 of the elongate body 120. The suture 400 may extend over cutting slot 117 on the underside 107 of the elongate body 120. On the topside 109 of the distal end 104, the suture 400 may enter the two side grooves below the deck 108 such that the suture 400 will tension the adjunct (not shown in FIGS. 9A and 9B) downward on to the deck 108 when the suture is provided through the longitudinal groove and on top of the mesh layer of the adjunct. The distal end 104 may further comprise guide ledges 136 to guide the suture 400 into the longitudinal groove of the adjunct.

With reference to FIGS. 10A and 10B, in some examples, the distal end 104 of the elongate body 120 comprises two side grooves 126 and a post 128 provided distal to the side grooves 126 to secure the suture 400 to the distal end of the staple cartridge. On the underside 107 of the distal end, the suture 400 may extend over cutting slot 117 provided between the two side grooves 126. In some examples, the post 128 centers the ends of the suture such that the suture 400 and is centered when extending into the longitudinal groove of the implantable adjunct (not shown in FIGS. 10A and 10B) from the post. In some examples, the two side groove 126 comprise an additional notch 127 to further secure the suture as it is wrapped toward the over the topside 109 and toward the post 128. In some examples, the post 128 is lower than the deck 108 such that the suture 400 will tension the adjunct (not shown in FIGS. 10A and 10B) downward on to the deck 108 when the suture is provided through the longitudinal groove and on top of the mesh layer of the adjunct.

FIGS. 11 and 12A-12G depict a routing method for securing a suture 400 having a first end 402 and a second end 404. The routing method may be carried out by a user (such as an assembler) or a pair of robotic arms, each arm manipulating one of the ends of the suture.

Figure 12B:
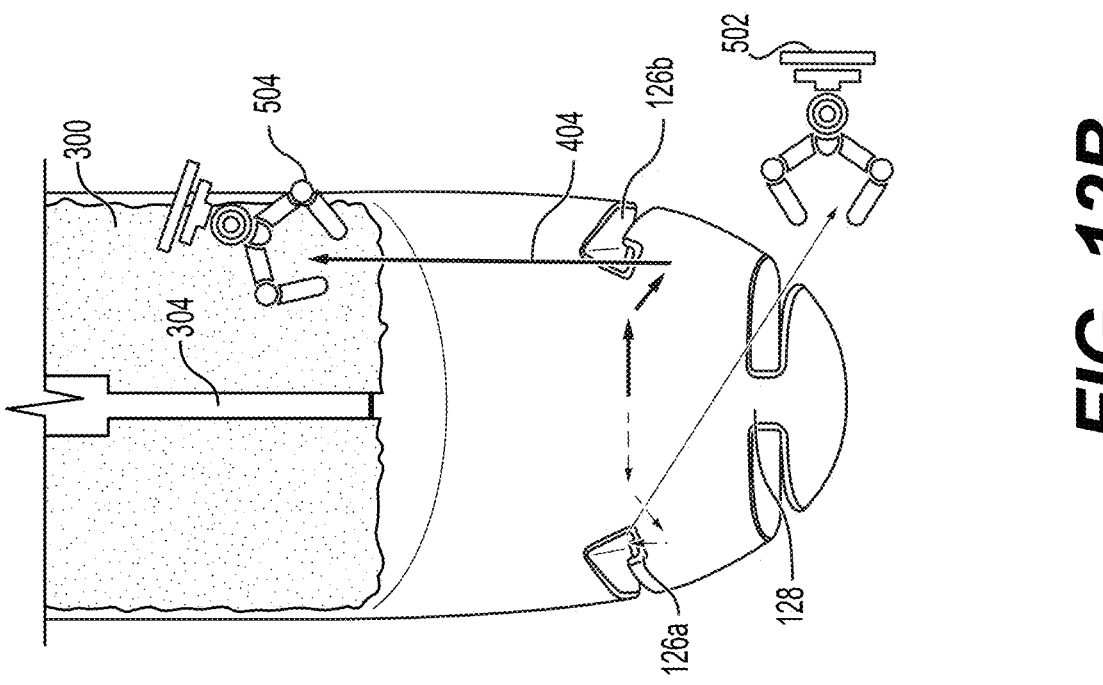
FIGS. 12A-12G depict a method of coupling a suture to of a distal end of an example staple cartridge, according to aspects of the present disclosure.
Figure 12A:
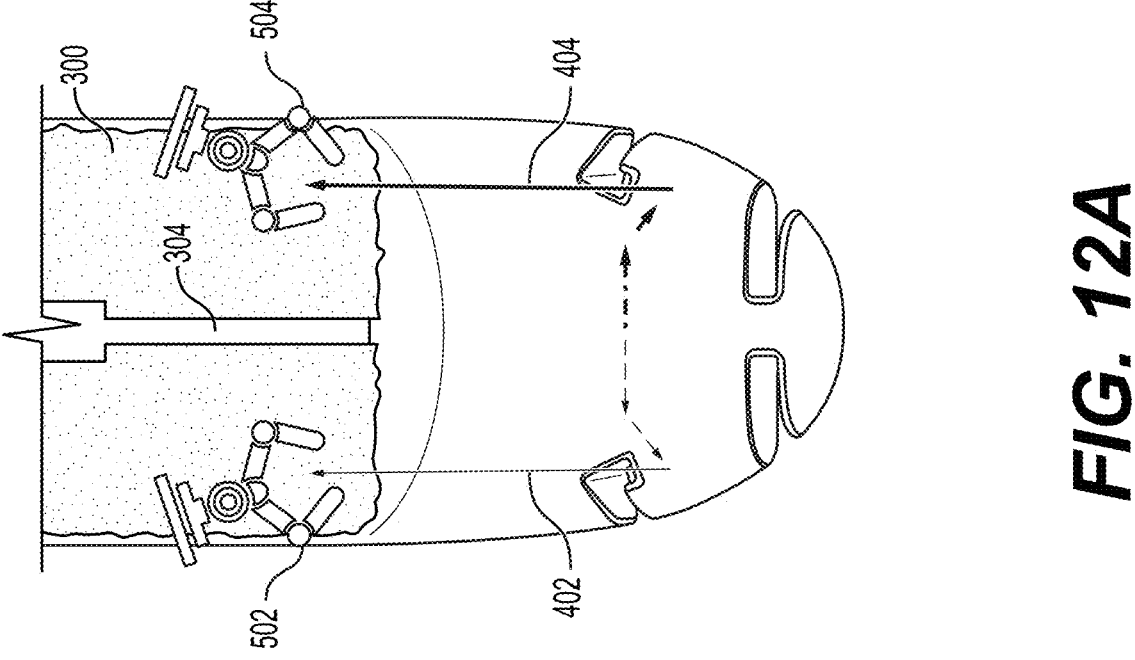
Figure 12D:
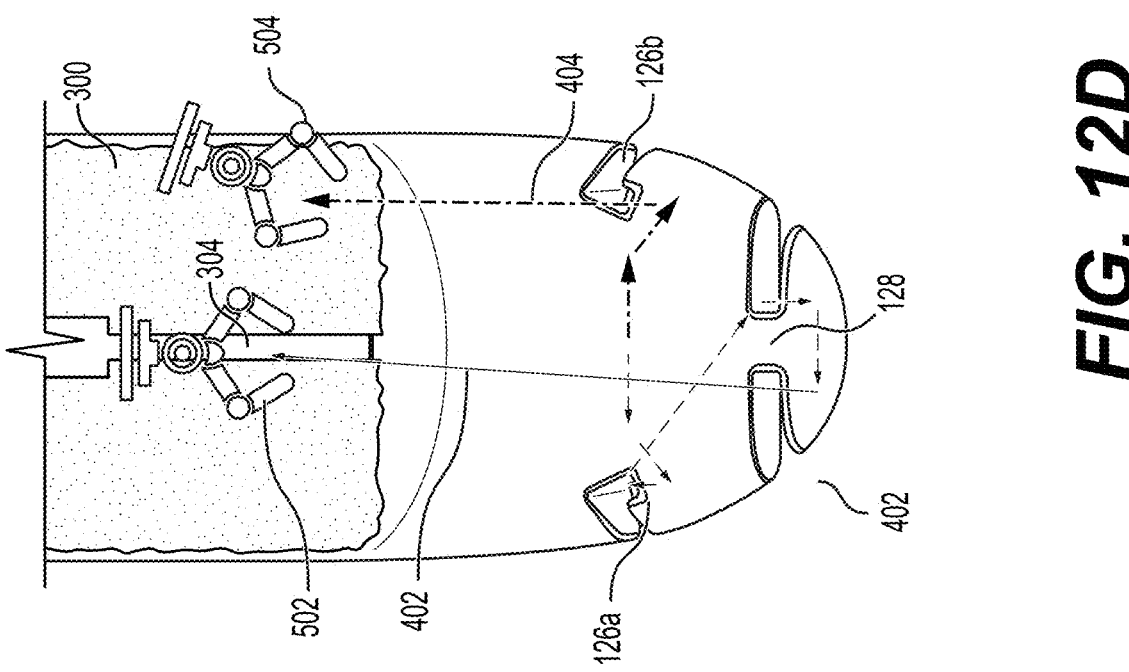
Figure 12C:
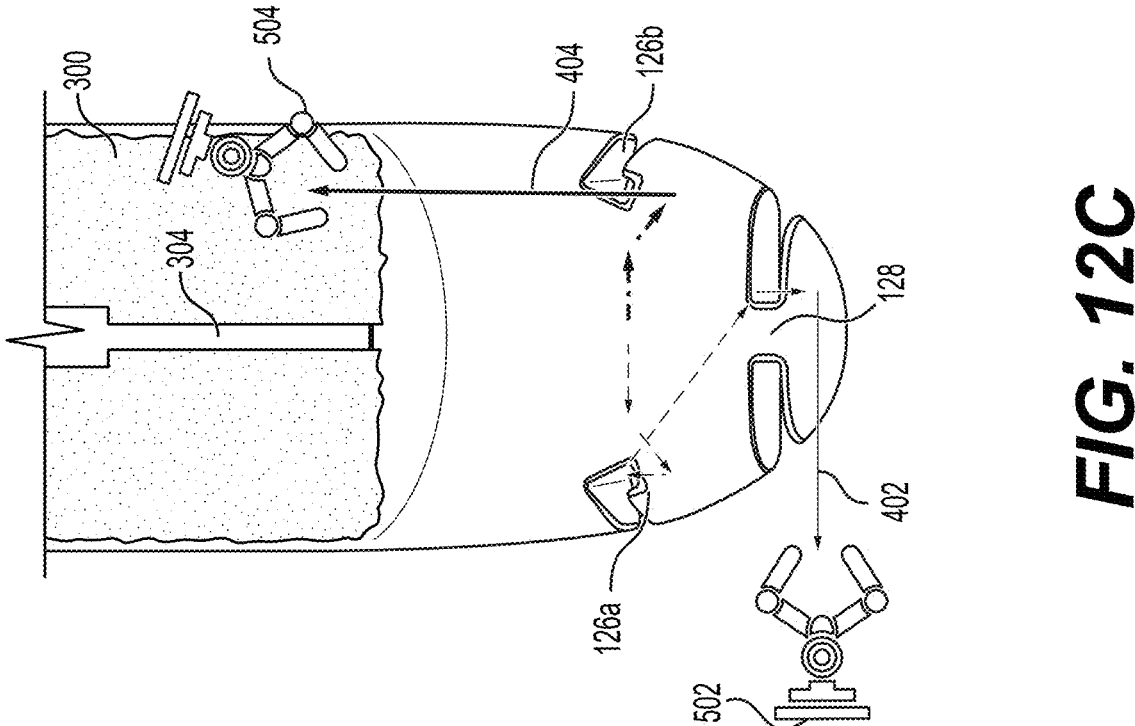
Figures 12E, 12F, 12G:
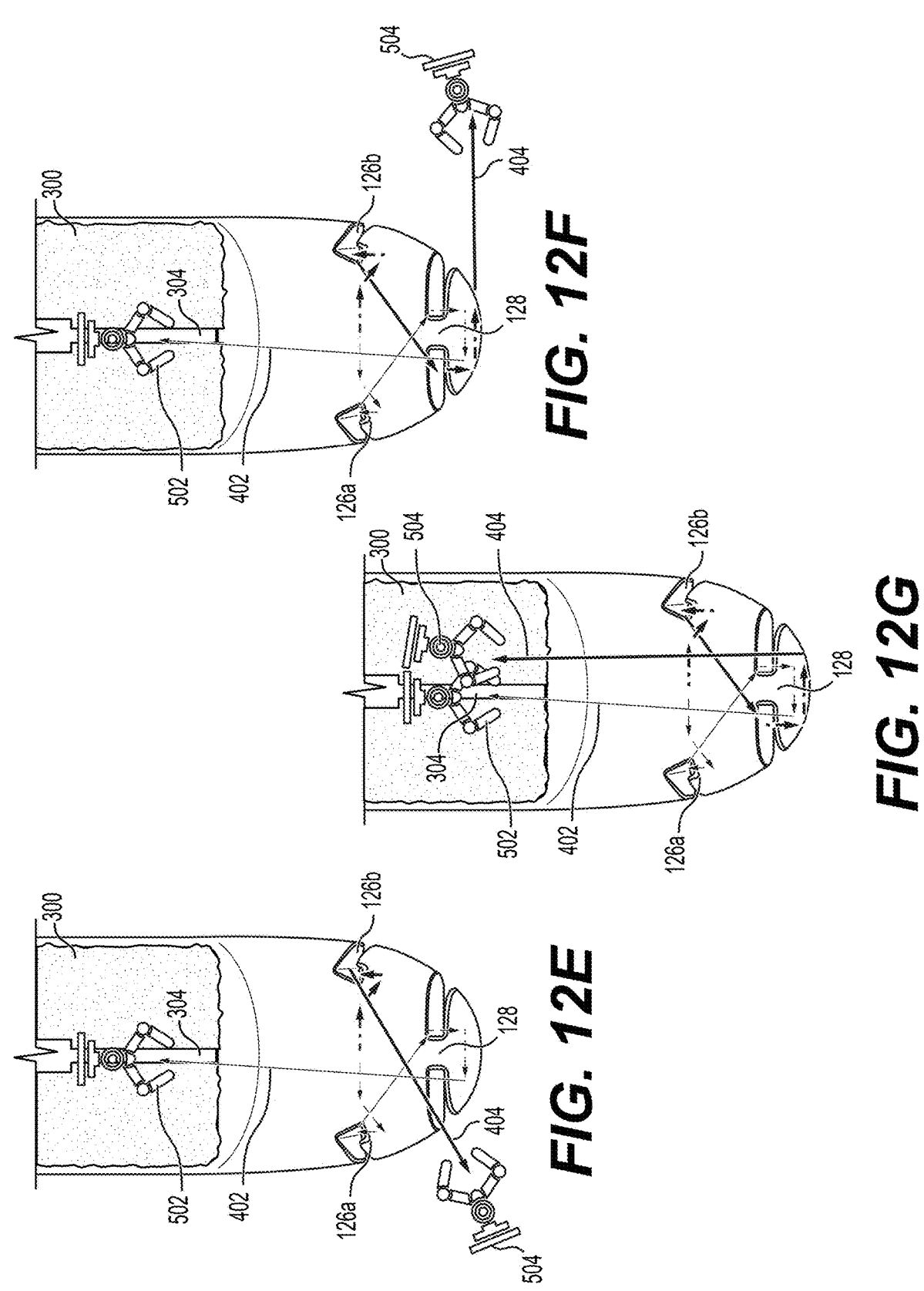

With reference to FIGS. 12A-12G, in some examples, a method for securing a suture 400 to a distal end 104 of the elongate body 120 comprises a first step of wrapping the suture 400 around an underside of the distal end 104 of the elongate body 120, such that the suture 400 extends over a cutting slot (e.g., cutting slot 117 depicted in FIGS. 8A, 9B, and 10B provided on the underside of the distal end 104 of the elongate body), advancing a first end 402 of the suture 400 through a first side groove 126a, and advancing a second end 404 of the suture 400 through a second side groove 126b, as depicted in FIG. 12A. A second step, according to some examples, comprises bringing the first end 402 of the suture 400 to post 128, as depicted in FIG. 12B. A third step, according to some examples, comprises wrapping the first end 402 of the suture 400 around post 128, as depicted in FIG. 12C. A fourth step, according to some examples, comprises positioning the first end 402 of the suture 400 through the longitudinal groove and onto the mesh layer of the implantable adjunct (not shown in FIGS. 12A-12G), as depicted in FIG. 12D. A fifth step, according to some examples, comprises bringing the second end 404 of the suture 400 to post 128, as depicted in FIG. 12E. A sixth step, according to some examples, comprises wrapping the second end 404 of the suture 400 around post 128, as depicted in FIG. 12F. A seventh step, according to some examples, comprises positioning the second end 404 of the suture 400 through the longitudinal groove and onto the mesh layer of the implantable adjunct (not shown in FIGS. 12A-12G), as depicted in FIG. 12G.

In some examples, the method of securing the suture to a distal end of the cartridge is carried out by a pair of robotic arms. In some examples, a first robotic arm 502 grips the first end 402 of the at least one suture 400, advances the first end 402 through the first side groove 126a, wraps the first end 402 around the post 128, and positions the first end 402 through the longitudinal groove and onto the mesh layer of the implantable adjunct. In some examples, a second robotic arm 504 grips the second end 404 of the at least one suture 400, advances the second end 404 through the second side groove 126b, wraps the second end 404 around the post 128, and positions the second end 404 through the longitudinal groove of the mesh layer of the implantable adjunct.

Examples of the present disclosure can be implemented by any of the following numbered clauses:

Clause 1: A staple cartridge (100), comprising: an elongate body (120), the elongate body (120) comprising a longitudinal slot (105) extending along a longitudinal axis (106) from a proximal end (102) toward a distal end (104) of the elongate body (120), the elongate body further comprising a deck (108), and a plurality of staple pockets (110), each of the staple pockets (110) accessible via an opening (112) in the deck (108); and an implantable adjunct (300) removably secured to the deck (108) by at least one suture (400), the at least one suture (400) provided within a longitudinal groove (304) of the implantable adjunct (300), the longitudinal groove (304) aligned with the longitudinal slot (105) of the elongate body (120), wherein the at least one suture (400) is secured at each of the proximal end (102) and distal end (104) of the elongate body (120).

Clause 2: The staple cartridge (100) of Clause 1, further comprising a pan (114), the pan (114) comprising hooks (116) securing the at least one suture (400) at the proximal end (102) of the elongate body (120).

Clause 3: The staple cartridge (100) of Clause 1 or 2, wherein the proximal end (102) of the elongate body (120) further comprises a suture guide (132) directing the at least one suture (400) into the longitudinal groove (304) of the implantable adjunct (300).

Clause 4: The staple cartridge (100) of Clause 3, wherein the suture guide (132) comprises a bottom surface (134) angled relative to the deck (108) at an angle (O).

Clause 5: The staple cartridge (100) of Clause 1, wherein the at least one suture (400) comprises a sleeve (410) attached onto at least one end of the at least one suture (400).

Clause 6: The staple cartridge (100) of Clause 5, wherein the proximal end (102) of the elongate body (120) further comprises a recess (144) to secure the sleeve (410) to the elongate body (120).

Clause 7: The staple cartridge (100) of Clause 6, wherein the recess (144) is sized to form a press-fit or an interference fit with the sleeve (410).

Clause 8: The staple cartridge (100) of Clause 1, wherein the proximal end (102) of the elongate body (120) further comprises a cavity (154) to receive a collet (420), the collet (420) having a first opening (422) to receive the at least one suture (400) therethrough and restrict the at least one suture (400) from sliding back through the first opening (422).

Clause 9: The staple cartridge (100) of Clause 8, wherein the cavity (422) tapers inward toward the longitudinal slot (105) such that the first opening (422) of the collet (420) clamps onto the at least one suture (400) as the collet (420) moves toward the longitudinal slot (105).

Clause 10: The staple cartridge (100) of any one of Clauses 1 to 9, wherein the distal end (104) comprises a cutting slot (117) on an underside (107) of the elongate body (120), wherein the at least one suture (400) extends across the cutting slot (117) thereby forming a space between the underside (107) of the elongate body (120) and the at least one suture (400) to accommodate a cutting instrument.

Clause 11: The staple cartridge (100) of Clause 10, wherein the distal end (104) further comprises two through holes (124) extending through the distal end (104) of the elongate body (120), wherein the at least one suture (400) passes through the through holes (124) from a topside (109) to the underside (107) of the elongate body (120) and across the cutting slot (117).

Clause 12: The staple cartridge (100) of Clause 10, wherein the distal end (104) of the elongate body (120) further comprises two side grooves (126), wherein the at least one suture (400) is looped around the two side grooves (126) securing the at least one suture (400) to the distal end (104) of the elongate body (120).

Clause 13: The staple cartridge (100) of Clause 12, further comprising a post (128) provided distal to the two side grooves (126) wherein the at least one suture (400) wraps around the post (128) to secure the at least one suture (400) to the distal end (104) of the elongate body (120).

Clause 14: The staple cartridge (100) of Clause 13, wherein the at least one suture (400) extends from the post (128) and into the longitudinal groove (304) of the implantable adjunct (300).

Clause 15: The staple cartridge (100) of any one of Clauses 10 to 14, wherein the distal end (104) of the elongate body (120) further comprises a guide ledge (136) directing the at least one suture (400) into the longitudinal groove (304) of the implantable adjunct (300).

Clause 16: The staple cartridge (100) of any one of Clauses 1 to 15, wherein the implantable adjunct (300) comprises a mesh layer (302), and wherein the at least one suture (400) rests on top of the mesh layer (302) when provided in the longitudinal groove (304) to secure the implantable adjunct (300) to the deck (108) of the elongate body (120) of the staple cartridge (100).

Clause 17: The staple cartridge (100) of any one of Clauses 1 to 16, wherein the at least one suture (400) is biased to one side of the longitudinal slot (105) of the elongate body (120).

Clause 18: A method for securing an implantable adjunct (300) to a deck (108) of an elongate body (120) of a staple cartridge (100) comprising: placing implantable adjunct (300) onto the deck (108) of the elongate body (120); securing at least one suture (400) to a distal end (104) of the elongate body (120); advancing the at least one suture (400) through a longitudinal groove (304) and onto a mesh layer (302) of the implantable adjunct (300); and securing the at least one suture (400) to a proximal end (102) of the elongate body (120) such that the at least one suture (400) provides a tension force onto the mesh layer (302) of the implantable adjunct (300) securing the implantable adjunct (300) to the deck of the elongate body (120).

Clause 19: The method of Clause 18, wherein securing the at least one suture (400) to the distal end (104) of the elongate body (120) comprises: wrapping the at least one suture (400) around an underside (107) of the distal end (104) of the elongate body (120), such that the at least one suture (400) extends over a cutting slot (117) provided on the underside (107) of the distal end (104) of the elongate body (120); advancing a first end (402) of the at least one suture (400) through a first side groove (126a) provided on the distal end (104) of the elongate body (120); advancing a second end (404) of the at least one suture (400) through a second side groove (126b) provided on the distal end (104) of the elongate body (120); wrapping the first end (402) of the at least one suture (400) around a post (128); positioning the first end (402) of the at least one suture (400) through the longitudinal groove (304) and onto the mesh layer (302) of the implantable adjunct (300); wrapping the second end (404) of the at least one suture (400) around the post (128); and positioning the second end (404) of the at least one suture (400) through the longitudinal groove (304) and onto the mesh layer (302) of the implantable adjunct (300).

Clause 20: The method of Clause 19, wherein a first robotic arm (502) grips the first end (402) of the at least one suture (400), advances the first end (402) through the first side groove (126a), wraps the first end (402) around the post (128), and positions the first end (402) through the longitudinal groove (304) and onto the mesh layer (302) of the implantable adjunct (300); and a second robotic arm (504) grips the second end (404) of the at least one suture (400), advances the second end (404) through the second side groove (126b), wraps the second end (404) around the post (128), and positions the second end (404) through the longitudinal groove (304) and onto the mesh layer (302) of the implantable adjunct (300).

The invention is not necessarily limited to the examples described, which can be varied in construction and detail. The terms "distal" and "proximal" are used throughout the preceding description and are meant to refer to a positions and directions relative to the handle of surgical instrument 200. As such, "distal" or distally" refer to a position distant to or a direction away from the handle of surgical instrument 200 (i.e., a direction toward a patient). Similarly, "proximal" or "proximally" refer to a position near or a direction towards the robotic arm. Furthermore, the singular forms "a," "an," and "the" include plural referents unless the context clearly dictates otherwise. Furthermore, the use of "couple", "coupled", or similar phrases should not be construed as being limited to a certain number of components or a particular order of components unless the context clearly dictates otherwise.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g., "about 90%" may refer to the range of values from 80.1% to 99.9%.

In describing example embodiments, terminology has been resorted to for the sake of clarity. As a result, not all possible combinations have been listed, and such variants are often apparent to those of skill in the art and are intended to be within the scope of the claims which follow. It is intended that each term contemplates its broadest meaning as understood by those skilled in the art and includes all technical equivalents that operate in a similar manner to accomplish a similar purpose without departing from the scope and spirit of the invention. It is also to be understood that the mention of one or more steps of a method does not preclude the presence of additional method steps or intervening method steps between those steps expressly identified. Similarly, some steps of a method can be performed in a different order than those described herein without departing from the scope of the disclosed technology.

What is claimed is:

1. A staple cartridge, comprising:
an elongate body, the elongate body comprising longitudinal slot extending along a longitudinal axis from a proximal end toward a distal end of the elongate body, the elongate body further comprising a deck, and a plurality of staple pockets, each of the staple pockets accessible via an opening in the deck; and
an implantable adjunct removably secured to the deck by at least one suture, the at least one suture extending parallel to and within a longitudinal groove of the implantable adjunct, the longitudinal groove aligned with the longitudinal slot of the elongate body,
wherein the at least one suture is secured at each of the proximal end and distal end of the elongate body.

2. The staple cartridge of claim 1, further comprising a pan, the pan comprising hooks securing the at least one suture at the proximal end of the elongate body.

3. The staple cartridge of claim 2, wherein the proximal end of the elongate body further comprises a suture guide directing the at least one suture into the longitudinal groove of the implantable adjunct.

4. The staple cartridge of claim 3, wherein the suture guide comprises a bottom surface angled relative to the deck at an angle (θ).

5. The staple cartridge of claim 1, wherein the at least one suture comprises a sleeve attached onto at least one end of the at least one suture.

6. The staple cartridge of claim 5, wherein the proximal end of the elongate body further comprises a recess to secure the sleeve to the elongate body.

7. The staple cartridge of claim 6, wherein the recess is sized to form a press-fit or an interference fit with the sleeve.

8. The staple cartridge of claim 1, wherein the proximal end of the elongate body further comprises a cavity to receive a collet, the collet having a first opening to receive the at least one suture therethrough and restrict the at least one suture from sliding back through the first opening.

9. The staple cartridge of claim 8, wherein the cavity tapers inward toward the longitudinal slot such that the first opening of the collet clamps onto the at least one suture as the collet moves toward the longitudinal slot.

10. The staple cartridge of claim 1, wherein the distal end comprises a cutting slot on an underside of the elongate body, wherein the at least one suture extends across the cutting slot thereby forming a space between the underside of the elongate body and the at least one suture to accommodate a cutting instrument.

11. The staple cartridge of claim 10, wherein the distal end further comprises two through holes extending through the distal end of the elongate body, wherein the at least one suture passes through the through holes from a topside to the underside of the elongate body and across the cutting slot.

12. The staple cartridge of claim 10, wherein the distal end of the elongate body further comprises two side grooves, wherein the at least one suture is looped around the two side grooves securing the at least one suture to the distal end of the elongate body.

13. The staple cartridge of claim 12, further comprising a post provided distal to the two side grooves wherein the at least one suture wraps around the post to secure the at least one suture to the distal end of the elongate body.

14. The staple cartridge of claim 13, wherein the at least one suture extends from the post and into the longitudinal groove of the implantable adjunct.

15. The staple cartridge of claim 10, wherein the distal end of the elongate body further comprises a guide ledge directing the at least one suture into the longitudinal groove of the implantable adjunct.

16. The staple cartridge of claim 1, wherein the at least one suture is biased to one side of the longitudinal slot of the elongate body.

17. The staple cartridge of claim 1, wherein the implantable adjunct comprises a mesh layer, and wherein the at least one suture rests on top of the mesh layer when provided in the longitudinal groove to secure the implantable adjunct to the deck of the elongate body of the staple cartridge.

18. A staple cartridge, comprising:
an elongate body, the elongate body comprising longitudinal slot extending along a longitudinal axis from a proximal end toward a distal end of the elongate body, the elongate body further comprising a deck, and a plurality of staple pockets, each of the staple pockets accessible via an opening in the deck; and
an implantable adjunct removably secured to the deck by at least one suture, the at least one suture provided within a longitudinal groove of the implantable adjunct, the longitudinal groove aligned with the longitudinal slot of the elongate body,
wherein the at least one suture is secured at each of the proximal end and distal end of the elongate body, and
wherein the implantable adjunct comprises a mesh layer, and wherein the at least one suture rests on top of the mesh layer when provided in the longitudinal groove to secure the implantable adjunct to the deck of the elongate body of the staple cartridge.

19. A method for securing an implantable adjunct to a deck of an elongate body of a staple cartridge comprising:
placing implantable adjunct onto the deck the elongate body;
securing at least one suture to a distal end of the elongate body;
advancing the at least one suture through a longitudinal groove and onto a mesh layer of the implantable adjunct; and
securing the at least one suture to a proximal end of the elongate body such that the at least one suture provides a tension force onto the mesh layer of the implantable adjunct securing the implantable adjunct to the deck of the elongate body.

20. The method of claim 19, wherein securing the at least one suture to the distal end of the elongate body comprises:

wrapping the at least one suture around an underside of the distal end of the elongate body, such that the at least one suture extends over a cutting slot provided on the underside of the distal end of the elongate body;

advancing a first end of the at least one suture through a first side groove (126*a*) provided on the distal end of the elongate body;

advancing a second end of the at least one suture through a second side groove (126*b*) provided on the distal end of the elongate body;

wrapping the first end of the at least one suture around a post;

positioning the first end of the at least one suture through the longitudinal groove and onto the mesh layer of the implantable adjunct;

wrapping the second end of the at least one suture around the post; and positioning the second end of the at least one suture through the longitudinal groove and onto the mesh layer of the implantable adjunct.

21. The method of claim 20, wherein a first robotic arm grips the first end of the at least one suture, advances the first end through the first side groove, wraps the first end around the post, and positions the first end through the longitudinal groove and onto the mesh layer of the implantable adjunct; and a second robotic arm grips the second end of the at least one suture, advances the second end through the second side groove, wraps the second end around the post, and positions the second end through the longitudinal groove and onto the mesh layer of the implantable adjunct.

* * * * *